United States Patent [19]
Bayne et al.

[11] Patent Number: 5,994,300
[45] Date of Patent: Nov. 30, 1999

[54] VASCULAR ENDOTHELIAL CELL GROWTH FACTOR C SUBUNIT

[75] Inventors: Marvin L. Bayne, Westfield; Kenneth A. Thomas, Jr., Chatham Borough, both of N.J.

[73] Assignee: Merck & Co., Inc., Rahway, N.J.

[21] Appl. No.: 08/124,259

[22] Filed: Sep. 20, 1993

Related U.S. Application Data

[63] Continuation-in-part of application No. 07/676,436, Mar. 28, 1991, abandoned.

[51] Int. Cl.$^6$ .......................... A61K 38/00; A61K 35/34; A61K 38/24; C12P 21/06
[52] U.S. Cl. ..................... 514/12; 435/69.1; 435/252.3; 435/240.2; 435/320.1; 424/569; 530/350; 530/399
[58] Field of Search ................. 435/69.1, 252.3, 435/240.2, 320.1; 424/569; 530/350, 399; 514/12

[56] References Cited

FOREIGN PATENT DOCUMENTS

| | | |
|---|---|---|
| 0 259 953 | 3/1988 | European Pat. Off. . |
| 0 370 989 | 5/1990 | European Pat. Off. . |
| 0 399 816 | 11/1990 | European Pat. Off. . |
| 0 476 983 | 3/1992 | European Pat. Off. . |
| WO 90/13649 | 11/1990 | WIPO . |
| WO 91/02058 | 2/1991 | WIPO . |

OTHER PUBLICATIONS

Conn, G. et al., Proc. Natl. Acad. Sci. USA 87: 2628–2632 (1990).
Conn, G. et al., Proc. Natl. Acad. Sci. USA 87: 1323–1327 (1990).
Connolly, D. et al., J. Clin. Invest. 84: 1470–1478 (1989).
Frohman, M. et al., Proc. Natl. Acad. Sci. USA 85: 8998–9002 (1988).
Leung, D. et al., Science 246: 1306–1309 (1989).
Keck, P. et al., Science 246: 1309–1312 (1989).
Gospodarowicz, D. et al., Proc. Natl. Acad. Sci. USA 86: 7311–7315 (1989).
Laemmli, Nature 227: 680–685 (1970).
Connolly, D., J. Biol. Chem. 264: 20017–20024 (1989).
Ferrara and Henzel, Biochem. Biophys. Res. Comm. 161: 851–858 (1989).
Plouet, J. et al., EMBO Journal 8: 3801–3806 (1989).
Levy, A. et al., Growth Factors 2: 9–19 (1989).
Saiki, R. et al., Science 230: 1350–1354 (1985).
Conn, Endothelial Cell Growth Factors, Yeshiva University, 1987.
D. Maglione, et al., Proc. Natl. Acad. Sci., USA 88; pp. 9267–9271 (1991).
Leung et al. "Vascular endothelial growth factor . . . " *Science* 246: 1306–1309, Dec. 8, 1989.
Connolly et al. "Human Vascular Permeability Factor . . ." *J. B. C.* 264: 20017–20024, (1989).
Keck et al "Vascular Permeability Factor . . ." *Science* 246: 1309–1312, Dec. 8, 1989.

*Primary Examiner*—Robert A. Wax
*Assistant Examiner*—Hyosuk Kim
*Attorney, Agent, or Firm*—J. Mark Hand; Joanne M. Giesser; Jack L. Tribble

[57] ABSTRACT

Vascular endothelial cell growth factor C subunit DNA is prepared by polymerase chain reaction techniques. The DNA encodes a protein that may exist as either a heterodimer or homodimer. The protein is a mammalian vascular endothelial cell mitogen and as such is useful for the promotion of vascular development and repair. This unique growth factor is also useful in the promotion of tissue repair.

7 Claims, 27 Drawing Sheets

```
                                    p4238
81  CGG TGT GCG GGC TGC TGC AAT GAT GAA GCC CTG GAG TGC GTG CCC ACG TCG GAG AGC AAC
                                          90                                    100
    ARG-CYS-ALA-GLY-CYS-CYS-ASN-ASP-GLU-ALA-LEU-GLU-CYS-VAL-PRO-THR-SER-GLU-SER-ASN-
                                   L42
                                   V30 p4238
101 GTC ACT ATG CAG ATC ATG CGG ATC AAA CCT CAC CAA AGC CAG CAC ATA GGA GAG ATG AGC
                                          110                                   120
    VAL-THR-MET-GLN-ILE-MET-ARG-ILE-LYS-PRO-HIS-GLN-SER-GLN-HIS-ILE-GLY-GLU-MET-SER-
                                   L42
                                   V18A
                                        CB18-19
```

FIG. 1C

```
            ─────────────────────────── p4238 ───────────────────────────
    TTC CAG GAG TAC CCC GAT GAG ATA GAG TAT ATC TTC AAG CCG TCC TGT GTG CCC CTA ATG
    61                                  70                                       80
    PHE-GLN-GLU-TYR-PRO-ASP-GLU-ILE-GLU-TYR-ILE-PHE-LYS-PRO-SER-CYS-VAL-PRO-LEU-MET-
                            ↑ ↑ ↑ ↑ ↑
            ─────── L46 ───────

─────────────────────────── p4238 ───────────────────────────
    CGG TGT GCG GGC TGC TGC AAT GAT GAA GCC CTG GAG TGC GTG CCC ACG TCG GAG AGC AAC
    81                                  90                                      100
    ARG-CYS-ALA-GLY-CYS-CYS-ASN-ASP-GLU-ALA-LEU-GLU-CYS-VAL-PRO-THR-SER-GLU-SER-ASN-
                                    ─────────────────────── L46 ───────────────────────

─────────────────────────── p4238 ───────────────────────────
    GTC ACT ATG CAG ATC ATG CGG ATC AAA CCT CAC CAA AGC CAG CAC ATA GGA GAG ATG AGC
    101                                 110                                     120
    VAL-THR-MET-GLN-ILE-MET-ARG-ILE-LYS-PRO-HIS-GLN-SER-GLN-HIS-ILE-GLY-GLU-MET-SER-
                                    ─────────────────────── L46 ───────────────────────
```

FIG.2B

```
                                           ──────── p4238 ────────
TTC CTG CAG CAT AGC AGA TGT GAA TGC AGA CCA AAG AAA GAT AGA ACA AAG CCA GAA AAT
121                                                                          140
PHE-LEU-GLN-HIS-SER-ARG-CYS-GLU-CYS-ARG-PRO-LYS-LYS-ASP-ARG-THR-LYS-PRO-GLU-ASN-
                                                            ──────── L20 ────────
                                          ──────── pW-3 ────────
                          ─┤├─ p4238

CAC TGT GAG CCT TGT TCA GAG CGG AGA AAG CAT TTG TTT GTC CAA GAT CCG CAG ACG TGT
141                                                                          160
HIS-CYS-GLU-PRO-CYS-SER-GLU-ARG-ARG-LYS-HIS-LEU-PHE-VAL-GLN-ASP-PRO-GLN-THR-CYS
                                                                  ──── L30 ────
                         ──────── pW-3 ────────

AAA TGT TCC TGC AAA AAC ACA GAC TCG CGT TGC AAG GCG AGG CAG CTT GAG TTA AAC GAA
161                                                                          180
LYS-CYS-SER-CYS-LSY-ASN-THR-ASP-SER-ARG-CYS-LSY-ALA-ARG-GLN-LEU-GLU-LEU-ASN-GLU-
                                                               ─┤├─
 ──────── L30 ────────                   ──────── L26 ────────
```

FIG.2C

CGT ACT TGC AGA TGT GAC AAG CCA AGG CGG TGA (SEQ ID NO: 30)

181                              190

AAG-THR-CYS-ARG-CYS-ASP-LYS-PRO-ARG-ARG * (SEQ ID NO: 31)

```
        ATG CTG GCC ATG AAG CTG TTC ACT TGC TTC TTG CAG GTC CTA GCT GGG TTG
          1                                  10
        MET-LEU-ALA-MET-LYS-LEU-PHE-THR-CYS-PHE-LEU-GLN-VAL-LEU-ALA-GLY-LEU-

GCT GTA CAC TCC CAG GGG GCC CTG TCT GCT GGG AAC AAC TCA ACA GAA GTG GTG
                    20                              30
        ALA-VAL-HIS-SER-GLN-GLY-ALA-LEU-SER-ALA-GLY-ASN-ASN-SER-THR-GLU-VAL-VAL-
                                                        (L44)

CCT TTC AAT GAA GTG TGG GGC CGC AGC TAC TGC CGG CCA ATG GAG AAG CTG GTG TAC ATT
                        40                              50
        PRO-PHE-ASN-GLU-VAL-TRP-GLY-ARG-SER-TYR-CYS-ARG-PRO-MET-GLU-LYS-LEU-VAL-TYR-ILE-
                        (L44)
```

FIG. 3A

```
                                     ─────── pCV2 ───────
GCA GAT GAA CAC CCT AAT GAA GTG TCT CAT ATA TTC AGT CCG TCA TGT GTC CTT CTG AGT
                 60                          70
ALA-ASP-GLU-HIS-PRO-ASN-GLU-VAL-SER-HIS-ILE-PHE-SER-PRO-SER-CYS-VAL-LEU-LEU-SER-
                                         ──── L50 ────
                                     ─────── pCV2 ───────
CGC TGT AGT GGC TGC TGT GGT GAC GAG GGT CTG CAC TGT GTG GCG CTA AAG ACA GCC AAC
                 80                          90
ARG-CYS-SER-GLY-CYS-CYS-GLY-ASP-GLU-GLY-LEU-HIS-CYS-VAL-ALA-LEU-LYS-THR-ALA-[ASN]-
                                    ──── L50 ────
                                     ─────── pCV2 ───────
ATC ACT ATG CAG ATC TTA AAG ATT CCC CCC AAT CGG GAT CCA CAT TCC

FIG. 3C

——————————— pCV2 ———————————
ACA TTC TCT CAG GAT GTA CTC TGC GAA TGC AGG CCT ATT CTG GAG ACG ACA AAG GCA GAA
THR-PHE-SER-GLN-ASP-VAL-LEU-CYS-GLU-CYS-ARG-PRO-ILE-LEU-GLU-THR-THR-LYS-ALA-GLU-
          120                                        130                              (L44)

——————————— pCV2 ———————————
AGG AGG AAA ACC AAG GGG AAG AGG AAG CAA AGC AAA ACC CCA CAG ACT GAG GAA CCC CAC
ARG-ARG-LYS-THR-LYS-GLY-LYS-ARG-LYS-GLN-SER-LYS-THR-PRO-GLN-THR-GLU-GLU-PRO-HIS-
              140                                          150
                                                                                    L26

CTG TGA   (SEQ ID NO: 38)
158
LEU *     (SEQ ID NO: 39)

```
ACCA ATG AAC TTT CTG CTC TCT TGG GTG CAC TGG ACC CTG GCT TTA CTG   49
     Met Asn Phe Leu Leu Ser Trp Val His Trp Thr Leu Ala Leu Leu
                       5                  10                 15

CTG TAC CTC CAC CAT GCC AAG TGG TCC CAG GCT GCA CCC ACG ACA         94
Leu Tyr Leu His His Ala Lys Trp Ser Gln Ala Ala Pro Thr Thr
                20                  25                 30

GAA GGG GAG CAG AAA GCC CAT GAA GTG GTG AAG TTC ATG GAC GTC        139
Glu Gly Glu Gln Lys Ala His Glu Val Val Lys Phe Met Asp Val
                35                  40                 45

TAC CAG CGC AGC TAT TGC CGT CCG ATT GAG ACC CTG GTG GAC ATC        184
Tyr Gln Arg Ser Tyr Cys Arg Pro Ile Glu Thr Leu Val Asp Ile
                50                  55                 60

TTC CAG GAG TAC CCC GAT GAG ATA GAG TAT ATC TTC AAG CCG TCC        229
Phe Gln Glu Tyr Pro Asp Glu Ile Glu Tyr Ile Phe Lys Pro Ser
                65                  70                 75

TGT GTG CCC CTA ATG CGG TGT GCG GGC TGC TGC AAT GAT GAA GCC        274
Cys Val Pro Leu Met Arg Cys Ala Gly Cys Cys Asn Asp Glu Ala
                80                  85                 90

CTG GAG TGC GTG CCC ACG TCG GAG AGC AAC GTC ACT ATG CAG ATC        319
Leu Glu Cys Val Pro Thr Ser Glu Ser Asn Val Thr Met Gln Ile
                95                 100                105

ATG CGG ATC AAA CCT CAC CAA AGC CAG CAC ATA GGA GAG ATG AGC        364
Met Arg Ile Lys Pro His Gln Ser Gln His Ile Gly Glu Met Ser
               110                 115                120

TTC CTG CAG CAT AGC AGA TGT GAA TGC AGA CCA AAG AAA GAT AGA        409
Phe Leu Gln His Ser Arg Cys Glu Cys Arg Pro Lys Lys Asp Arg
               125                 130                135

ACA AAG CCA GAA AAA TGT GAC AAG CCA AGG CGG TGA   445  (SEQ ID NO: 32)
Thr Lys Pro Glu Lys Cys Asp Lys Pro Arg Arg            (SEQ ID NO: 33)
               140                 145
```

FIG. 4

```
AACC ATG AAC TTT CTG CTC TCT TGG GTG CAC TGG ACC CTG GCT TTA CTG  49
     Met Asn Phe Leu Leu Ser Trp Val His Trp Thr Leu Ala Leu Leu
                  5                  10                  15

CTG TAC CTC CAC CAT GCC AAG TGG TCC CAG GCT GCA CCC ACG ACA        94
Leu Tyr Leu His His Ala Lys Trp Ser Gln Ala Ala Pro Thr Thr
              20                  25                  30

GAA GGG GAG CAG AAA GCC CAT GAA GTG GTG AAG TTC ATG GAC GTC       139
Glu Gly Glu Gln Lys Ala His Glu Val Val Lys Phe Met Asp Val
              35                  40                  45

TAC CAG CGC AGC TAT TGC CGT CCG ATT GAG ACC CTG GTG GAC ATC       184
Tyr Gln Arg Ser Tyr Cys Arg Pro Ile Glu Thr Leu Val Asp Ile
              50                  55                  60

TTC CAG GAG TAC CCC GAT GAG ATA GAG TAT ATC TTC AAG CCG TCC       229
Phe Gln Glu Tyr Pro Asp Glu Ile Glu Tyr Ile Phe Lys Pro Ser
              65                  70                  75

TGT GTG CCC CTA ATG CGG TGT GCG GGC TGC TGC AAT GAT GAA GCC       274
Cys Val Pro Leu Met Arg Cys Ala Gly Cys Cys Asn Asp Glu Ala
              80                  85                  90

CTG GAG TGC GTG CCC ACG TCG GAG AGC AAC GTC ACT ATG CAG ATC       319
Leu Glu Cys Val Pro Thr Ser Glu Ser Asn Val Thr Met Gln Ile
              95                 100                 105

ATG CGG ATC AAA CCT CAC CAA AGC CAG CAC ATA GGA GAG ATG AGC       364
Met Arg Ile Lys Pro His Gln Ser Gln His Ile Gly Glu Met Ser
             110                 115                 120

TTC CTG CAG CAT AGC AGA TGT GAA TGC AGA CCA AAG AAA GAT AGA       409
Phe Leu Gln His Ser Arg Cys Glu Cys Arg Pro Lys Lys Asp Arg
             125                 130                 135

ACA AAG CCA GAA AAT CAC TGT GAG CCT TGT TCA GAG CGG AGA AAG       454
Thr Lys Pro Glu Asn His Cys Glu Pro Cys Ser Glu Arg Arg Lys
             140                 145                 150

CAT TTG TTT GTC CAA GAT CCG CAG ACG TGT AAA TGT TCC TGC AAA       499
His Leu Phe Val Gln Asp Pro Gln Thr Cys Lys Cys Ser Cys Lys
             155                 160                 165

AAC ACA GAC TCG CGT TGC AAG GCG AGG CAG CTT GAG TTA AAC GAA       544
Asn Thr Asp Ser Arg Cys Lys Ala Arg Gln Leu Glu Leu Asn Glu
             170                 175                 180

CGT ACT TGC AGA TGT GAC AAG CCA AGG CGG TGA                       577  (SEQ ID NO: 30)
Arg Thr Cys Arg Cys Asp Lys Pro Arg Arg                                (SEQ ID NO: 31)
             185                 190
```

FIG. 5

```
AACC ATG AAC TTT CTG CTC TCT TGG GTG CAC TGG ACC CTG GCT TTA CTG  49
     Met Asn Phe Leu Leu Ser Trp Val His Trp Thr Leu Ala Leu Leu
                  5                  10                      15

CTG TAC CTC CAC CAT GCC AAG TGG TCC CAG GCT GCA CCC ACG ACA  94
Leu Tyr Leu His His Ala Lys Trp Ser Gln Ala Ala Pro Thr Thr
                20                  25                  30

GAA GGG GAG CAG AAA GCC CAT GAA GTG GTG AAG TTC ATG GAC GTC 139
Glu Gly Glu Gln Lys Ala His Glu Val Val Lys Phe Met Asp Val
                35                  40                  45

TAC CAG CGC AGC TAT TGC CGT CCG ATT GAG ACC CTG GTG GAC ATC 184
Tyr Gln Arg Ser Tyr Cys Arg Pro Ile Glu Thr Leu Val Asp Ile
                50                  55                  60

TTC CAG GAG TAC CCC GAT GAG ATA GAG TAT ATC TTC AAG CCG TCC 229
Phe Gln Glu Tyr Pro Asp Glu Ile Glu Tyr Ile Phe Lys Pro Ser
                65                  70                  75

TGT GTG CCC CTA ATG CGG TGT GCG GGC TGC TGC AAT GAT GAA GCC 274
Cys Val Pro Leu Met Arg Cys Ala Gly Cys Cys Asn Asp Glu Ala
                80                  85                  90

CTG GAG TGC GTG CCC ACG TCG GAG AGC AAC GTC ACT ATG CAG ATC 319
Leu Glu Cys Val Pro Thr Ser Glu Ser Asn Val Thr Met Gln Ile
                95                  100                 105

ATG CGG ATC AAA CCT CAC CAA AGC CAG CAC ATA GGA GAG ATG AGC 364
Met Arg Ile Lys Pro His Gln Ser Gln His Ile Gly Glu Met Ser
                110                 115                 120

TTC CTG CAG CAT AGC AGA TGT GAA TGC AGA CCA AAG AAA GAT AGA 409
Phe Leu Gln His Ser Arg Cys Glu Cys Arg Pro Lys Lys Asp Arg
                125                 130                 135

ACA AAG CCA GAA AAA AAA TCA GTT CGA GGA AAG GGA AAG GGT CAA 454
Thr Lys Pro Glu Lys Lys Ser Val Arg Gly Lys Gly Lys Gly Gln
                140                 145                 150

AAA CGA AAG CGC AAG AAA TCC CGG TTT AAA TCC TGG AGC GTT CAC 499
Lys Arg Lys Arg Lys Lys Ser Arg Phe Lys Ser Trp Ser Val His
                155                 160                 165
```

FIG. 6A

```
TGT GAG CCT TGT TCA GAG CGG AGA AAG CAT TTG TTT GTC CAA GAT  544
Cys Glu Pro Cys Ser Glu Arg Arg Lys His Leu Phe Val Gln Asp
                170                 175                 180

CCG CAG ACG TGT AAA TGT TCC TGC AAA AAC ACA GAC TCG CGT TGC  589
Pro Gln Thr Cys Lys Cys Ser Cys Lys Asn Thr Asp Ser Arg Cys
                185                 190                 195

AAG GCG AGG CAG CTT GAG TTA AAC GAA CGT ACT TGC AGA TGT GAC  634
Lys Ala Arg Gln Leu Glu Leu Asn Glu Arg Thr Cys Arg Cys Asp
                200                 205                 210

AAG CCA AGG CGG TGA     649      (SEQ ID NO: 34)
Lys Pro Arg Arg                  (SEQ ID NO: 35)
```

FIG.6B

```
ATG CTG GCC ATG AAG CTG TTC ACT TGC TTC TTG CAG GTC CTA GCT      45
Met Leu Ala Met Lys Leu Phe Thr Cys Phe Leu Gln Val Leu Ala
                 5                  10                 15

GGG TTG GCT GTG CAC TCC CAG GGG GCC CTG TCT GCT GGG AAC AAC      90
Gly Leu Ala Val His Ser Gln Gly Ala Leu Ser Ala Gly Asn Asn
                20                  25                 30

TCA ACA GAA ATG GAA GTG GTG CCT TTC AAT GAA GTG TGG GGC CGC     135
Ser Thr Glu Met Glu Val Val Pro Phe Asn Glu Val Trp Gly Arg
                35                  40                 45

AGC TAC TGC CGG CCA ATG GAG AAG CTG GTG TAC ATT GCA GAT GAA     180
Ser Tyr Cys Arg Pro Met Glu Lys Leu Val Tyr Ile Ala Asp Glu
                50                  55                 60

CAC CCT AAT GAA GTG TCT CAT ATA TTC AGT CCG TCA TGT GTC CTT     225
His Pro Asn Glu Val Ser His Ile Phe Ser Pro Ser Cys Val Leu
                65                  70                 75

CTG AGT CGC TGT AGT GGC TGC TGT GGT GAC GAG GGT CTG CAC TGT     270
Leu Ser Arg Cys Ser Gly Cys Cys Gly Asp Glu Gly Leu His Cys
                80                  85                 90

GTG GCG CTA AAG ACA GCC AAC ATC ACT ATG CAG ATC TTA AAG ATT     315
Val Ala Leu Lys Thr Ala Asn Ile Thr Met Gln Ile Leu Lys Ile
                95                 100                105

CCC CCC AAT CGG GAT CCA CAT TCC TAC GTG GAG ATG ACA TTC TCT     360
Pro Pro Asn Arg Asp Pro His Ser Tyr Val Glu Met Thr Phe Ser
               110                 115                120

CAG GAT GTA CTC TGC GAA TGC AGG CCT ATT CTG GAG ACG ACA AAG     405
Gln Asp Val Leu Cys Glu Cys Arg Pro Ile Leu Glu Thr Thr Lys
               125                 130                135

GCA GAA AGG TAA    417         (SEQ ID NO: 36)
Ala Glu Arg                    (SEQ ID NO: 37)
```

FIG.7

| | |
|---|---|
| ATG CTG GCC ATG AAG CTG TTC ACT TGC TTC TTG CAG GTC CTA GCT<br>Met Leu Ala Met Lys Leu Phe Thr Cys Phe Leu Gln Val Leu Ala<br>　　　　　　　　　5　　　　　　　　　　10　　　　　　　　　15 | 45 |
| GGG TTG GCT GTG CAC TCC CAG GGG GCC CTG TCT GCT GGG AAC AAC<br>Gly Leu Ala Val His Ser Gln Gly Ala Leu Ser Ala Gly Asn Asn<br>　　　　　　　　　20　　　　　　　　　25　　　　　　　　　30 | 90 |
| TCA ACA GAA ATG GAA GTG GTG CCT TTC AAT GAA GTG TGG GGC CGC<br>Ser Thr Glu Met Glu Val Val Pro Phe Asn Glu Val Trp Gly Arg<br>　　　　　　　　　35　　　　　　　　　40　　　　　　　　　45 | 135 |
| AGC TAC TGC CGG CCA ATG GAG AAG CTG GTG TAC ATT GCA GAT GAA<br>Ser Tyr Cys Arg Pro Met Glu Lys Leu Val Tyr Ile Ala Asp Glu<br>　　　　　　　　　50　　　　　　　　　55　　　　　　　　　60 | 180 |
| CAC CCT AAT GAA GTG TCT CAT ATA TTC AGT CCG TCA TGT GTC CTT<br>His Pro Asn Glu Val Ser His Ile Phe Ser Pro Ser Cys Val Leu<br>　　　　　　　　　65　　　　　　　　　70　　　　　　　　　75 | 225 |
| CTG AGT CGC TGT AGT GGC TGC TGT GGT GAC GAG GGT CTG CAC TGT<br>Leu Ser Arg Cys Ser Gly Cys Cys Gly Asp Glu Gly Leu His Cys<br>　　　　　　　　　80　　　　　　　　　85　　　　　　　　　90 | 270 |
| GTG GCG CTA AAG ACA GCC AAC ATC ACT ATG CAG ATC TTA AAG ATT<br>Val Ala Leu Lys Thr Ala Asn Ile Thr Met Gln Ile Leu Lys Ile<br>　　　　　　　　　95　　　　　　　　　100　　　　　　　　　105 | 315 |
| CCC CCC AAT CGG GAT CCA CAT TCC TAC GTG GAG ATG ACA TTC TCT<br>Pro Pro Asn Arg Asp Pro His Ser Tyr Val Glu Met Thr Phe Ser<br>　　　　　　　　　110　　　　　　　　　115　　　　　　　　　120 | 360 |
| CAG GAT GTA CTC TGC GAA TGC AGG CCT ATT CTG GAG ACG ACA AAG<br>Gln Asp Val Leu Cys Glu Cys Arg Pro Ile Leu Glu Thr Thr Lys<br>　　　　　　　　　125　　　　　　　　　130　　　　　　　　　135 | 405 |
| GCA GAA AGG AGG AAA ACC AAG GGG AAG AGG AAG CAA AGC AAA ACC<br>Ala Glu Arg Arg Lys Thr Lys Gly Lys Arg Lys Gln Ser Lys Thr<br>　　　　　　　　　140　　　　　　　　　145　　　　　　　　　150 | 450 |
| CCA CAG ACT GAG GAA CCC CAC CTG TGA　　　477　　(SEQ ID NO: 38)<br>Pro Gln Thr Glu Glu Pro His Leu　　　　　　　　(SEQ ID NO: 39)<br>　　　　　　　　　155 | |

FIG. 8

```
ATG CCG GTC ATG AGG CTG TTC CCT TGC TTC CTG CAG CTC CTG GCC    45
Met Pro Val Met Arg Leu Phe Pro Cys Phe Leu Gln Leu Leu Ala
             5                  10                  15

GGG CTG GCG CTG CCT GCT GTG CCC CCC CAG CAG TGG GCC TTG TCT    90
Gly Leu Ala Leu Pro Ala Val Pro Pro Gln Gln Trp Ala Leu Ser
             20                  25                  30

GCT GGG AAC GGC TCG TCA GAG GTG GAA GTG GTA CCC TTC CAG GAA    135
Ala Gly Asn Gly Ser Ser Glu Val Glu Val Val Pro Phe Gln Glu
             35                  40                  45

GTG TGG GGC CGC AGC TAC TGC CGG GCG CTG GAG AGG CTG GTG GAC    180
Val Trp Gly Arg Ser Tyr Cys Arg Ala Leu Glu Arg Leu Val Asp
             50                  55                  60

GTC GTG TCC GAG TAC CCC AGC GAG GTG GAG CAC ATG TTC AGC CCA    225
Val Val Ser Glu Tyr Pro Ser Glu Val Glu His Met Phe Ser Pro
             65                  70                  75

TCC TGT GTC TCC CTG CTG CGC TGC ACC GGC TGC TGC GGC GAT GAG    270
Ser Cys Val Ser Leu Leu Arg Cys Thr Gly Cys Cys Gly Asp Glu
             80                  85                  90

AAT CTG CAC TGT GTG CCG GTG GAG ACG GCC AAT GTC ACC ATG CAG    315
Asn Leu His Cys Val Pro Val Glu Thr Ala Asn Val Thr Met Gln
             95                  100                 105

CTC CTA AAG ATC CGT TCT GGG GAC CGG CCC TCC TAC GTG GAG CTG    360
Leu Leu Lys Ile Arg Ser Gly Asp Arg Pro Ser Tyr Val Glu Leu
             110                 115                 120

ACG TTC TCT CAG CAC GTT CGC TGC GAA TGC CGG CCT CTG CGG GAG    405
Thr Phe Ser Gln His Val Arg Cys Glu Cys Arg Pro Leu Arg Glu
             125                 130                 135

AAG ATG AAG CCG GAA AGG AGG AGA CCC AAG GGC AGG GGG AAG AGG    450
Lys Met Lys Pro Glu Arg Arg Arg Pro Lys Gly Arg Gly Lys Arg
             140                 145                 150

AGG AGA GAG AAG TAG    465    (SEQ ID NO: 40)
Arg Arg Glu Lys               (SEQ ID NO: 41)
```

FIG. 9

```
  1    ATG CCG GTC ATG AGG CTG TTC CCT TGC TTC CTG CAG CTC CTG CTG GCC GGG CTG GCG CTG CCT GCT
       Met Pro Val Met Arg Leu Phe Pro Cys Phe Leu Gln Leu Leu Leu Ala Gly Leu Ala Leu Pro Ala

64    GTG CCC CCC CAG CAG CTC GCC TTG TCT GCT GGG AAC GGC TCA GAG GTC GAA GTC GTA CCC
       Val Pro Pro Gln Gln Leu Ala Leu Ser Ala Gly Asn Gly Ser Glu Val Glu Val Val Pro

127    TTC CAG GAA GTG TGG GGC CGC AGC TAC TGC CGG GCG CTG GAG AGG CTG GTG GAC GTC GTG TCC
       Phe Gln Glu Val Trp Gly Arg Ser Tyr Cys Arg Ala Leu Glu Arg Leu Val Asp Val Val Ser

190    GAG TAC CCC AGC GAG GTG GAG CAC ATG TTC AGC CCA TCC TGT GTC CCG CTG CTG CGC TGC ACC
       Glu Tyr Pro Ser Glu Val Glu His Met Phe Ser Pro Ser Cys Val Pro Leu Leu Arg Cys Thr

253    GGC TGC TGC GGC GAT GAG AAT CTC CAC TGT GTG CCG GTG CCG GTG CAG ACG GCC AAT GTC ACC ATG CAG
       Gly Cys Cys Gly Asp Glu Asn Leu His Cys Val Pro Val Gln Thr Ala Asn Val Thr Met Gln

316    CTC CTA AAG ATC CGT TCT GGG GAC CGG GAG AAG ATC AAG CCG GAG AGG AGG CCC TAC GTG CTG ACC TTC TCT CAG CAC GTT
       Leu Leu Lys Ile Arg Ser Gly Asp Arg Glu Lys Ile Lys Pro Glu Arg Arg Pro Tyr Val Glu Leu Thr Phe Ser Gln His Val

379    CGC TGC GAA TGC CGG CCT CTG CGG GAG AAG ATG AAG CCC GAA AGG AGG AGA CCC AAG GGC AGG
       Arg Cys Glu Cys Arg Pro Leu Arg Glu Lys Met Lys Pro Glu Arg Arg Arg Pro Lys Gly Arg

442    GGG AAG AGG AGA GAG AGG AGG AAG AGG CAG ACA GAC CCA CAC CTG TGC GGC GAT GCT GTT CCC
       Gly Lys Arg Arg Glu Arg Arg Lys Arg Gln Arg Pro Thr Asp Cys His Leu Cys Gly Asp Ala Val Pro

505    CGG AGG TAA              (SEQ ID NO: 44)
       Arg Arg ***              (SEQ ID NO: 45)
```

FIG. 10

1   ATG CCG GTC ATG AGG CTG TTC CCT TGC TTC CTG CAG CTC CTG GCC GGG CTG GCG CCT GCT
    Met Pro Val Met Arg Leu Phe Pro Cys Phe Leu Gln Leu Leu Ala Gly Leu Ala Pro Ala

64  GTC CCC CCC CAG CAG TGC GCC TTG TCT GCT GGG AAC GGC TCA GAG GTG GAA GTG GTA CCC
    Val Pro Pro Gln Gln Cys Ala Leu Ser Ala Gly Asn Gly Ser Glu Val Glu Val Val Pro

127 TTC CAG GAA GTG TGC GGC CGC AGC TAC TGC CGG GCC CTC GAC AGG CTG GAC GTC GTG TCC
    Phe Gln Glu Val Cys Gly Arg Ser Tyr Cys Arg Ala Leu Glu Arg Leu Asp Val Val Ser

190 GAG TAC CCC AGC GAG GTG GAG CAC ATG TTC CAC CCA TCC AGC CCA TCC TGT GTC TCC CTC CTG CCC TGC ACC
    Glu Tyr Pro Ser Glu Val Glu His Met Phe Ser Pro Ser Cys Val Ser Leu Arg Cys Thr

253 GGC TGC GGC GAT GAG AAT CTG CAC TGT CGT GTG CCG GAG ACG GCC AAT GTC ACC ATG CAG
    Gly Cys Gly Asp Glu Asn Leu His Cys Val Pro Val Glu Thr Ala Asn Val Thr Met Gln

316 CTC CTA AAG ATC CGT TCT GGG GAC CGG CCC TAC GTG GAG CTG ACG TTC TCT CAG CAC GTT
    Leu Leu Lys Ile Arg Ser Gly Asp Arg Pro Tyr Val Glu Leu Thr Phe Ser Gln His Val

379 CGC TGC GAA TGC CGG CCT CTG CGG GAG AAG ATG AAG CCG GAA AGG TGC GGC GAT GCT GTT CCC
    Arg Cys Glu Cys Arg Pro Leu Arg Glu Lys Met Lys Pro Glu Arg Cys Gly Asp Ala Val Pro

442 CGG AGG TAA      (SEQ ID NO: 46)
    Arg Arg ***     (SEQ ID NO: 47)

FIG.11

VEGF A215

```
1    ATG AAC TTT CTG CTG TCT TGG GTG CAT TGG AGC CTT GCC TTG CTG CTC TAC CTC CAC CAT GCC AAG TGG TCC CAG
     Met Asn Phe Leu Leu Ser Trp Val His Trp Ser Leu Ala Leu Leu Leu Tyr Leu His His Ala Lys Trp Ser Gln

76   GCT GCA CCC ATG GCA GAA GGA GGA GGG CAG AAT CAT CAC GAA GTG GTG AAG TTC ATG GAT GTC TAT CAG CGC AGC
     Ala Ala Pro Met Ala Glu Gly Gly Gly Gln Asn His His Glu Val Val Lys Phe Met Asp Val Tyr Gln Arg Ser

151  TAC TGC CAT CCA ATC GAG ACC CTG GTG GAC ATC TTC CAG GAG TAC CCT GAT GAG ATC GAG TAC ATC TTC AAG CCA
     Tyr Cys His Pro Ile Glu Thr Leu Val Asp Ile Phe Gln Glu Tyr Pro Asp Glu Ile Glu Tyr Ile Phe Lys Pro

226  TCC TGT GTG CCC CTG ATG CGA TGC GGG GGC TGC TGC AAT GAC GAG GGC CTG GAG TGT GTG CCC ACT GAG GAG TCC
     Ser Cys Val Pro Leu Met Arg Cys Gly Gly Cys Cys Asn Asp Glu Gly Leu Glu Cys Val Pro Thr Glu Glu Ser

301  AAC ATC ACC ATG CAG ATT ATG CGG ATC AAA CCT CAC CAA GGC CAG CAC ATA GGA GAG ATG AGC TTC CTA CAG CAC
     Asn Ile Thr Met Gln Ile Met Arg Ile Lys Pro His Gln Gly Gln His Ile Gly Glu Met Ser Phe Leu Gln His

376  AAC AAA TGT GAA TGC AGA CCA AAG AAA GAT AGA GCA AGA CAA GAA AAA AAA TCA GTT CGA GGA AAG GGA AAG GGG
     Asn Lys Cys Glu Cys Arg Pro Lys Lys Asp Arg Ala Arg Gln Glu Lys Lys Ser Val Arg Gly Lys Gly Lys Gly

451  CAA AAA CGA AAG CGC AAG AAA TCC CGG TAT AAG TCC TGG AGC GTT CCC TGT GGG CCT TGC TCA GAG CGG AGA AAG
     Gln Lys Arg Lys Arg Lys Lys Ser Arg Tyr Lys Ser Trp Ser Val Pro Cys Gly Pro Cys Ser Glu Arg Arg Lys
```

FIG.12A

526 CAT TTG TTT GTA CAA GAT CCG CAG ACG TGT AAA AAC ACA GAC TCG CGT TGC AAG GCG AGG CAG
    His Leu Phe Val Gln Asp Pro Gln Thr Cys Lys Asn Thr Asp Ser Arg Cys Lys Ala Arg Gln    (SEQ ID NO: 48)
                                                                                            (SEQ ID NO: 49)

601 CTT GAG TTA AAC GAA CGT ACT TGC AGA TGT GAC AAG CCG AGG CGG TG
    Leu Glu Leu Asn Glu Arg Thr Cys Arg Cys Asp Lys Pro Arg Arg

… # VASCULAR ENDOTHELIAL CELL GROWTH FACTOR C SUBUNIT

RELATED APPLICATIONS

This application is a continuation in part of application Ser. No. 07/676,436 filed Mar. 28, 1991 now abandoned.

BACKGROUND OF THE INVENTION

A new class of cell-derived dimeric mitogens with apparently restricted specificity for vascular endothelial cells has recently been identified and generally designated vascular endothelial growth factors (VEGFs). The mitogen has been purified from: conditioned growth media of rat glioma cells, [Conn et al., Proc. Natl. Acad. Sci. USA 87: 1323–1327 (1990)]; conditioned growth media of bovine pituitary folliculo stellate cells [Ferrara and Henzel, Biochem. Biophys. Res. Comm. 161: 851–858 (1989) and Gospodarowicz et al., Proc. Natl. Acad. Sci. USA 86: 7311–7315 (1989)]. An endothelial cell growth factor isolated form mouse neuroblastoma cell line NB41 with an unreduced molecular mass of 43–51 kDa and a reduced mass of 23–29 kDa has been described by Levy et al., Growth Factors 2: 9–19 (1989). Connolly et al. (J. Biol. Chem. 264: 20017–20024 [1989]; J. Clin. Invest. 84: 1470–1478 [1989]) describe a human vascular permeability factor that stimulates vascular endothelial cells to divide in vitro and promotes the growth of new blood vessels when administered into healing rabbit bone grafts or rat corneas. An endothelial cell growth factor has been purified from the conditioned medium of the AtT-20 pituitary cell line by Plouet et al., EMBO Journal 8: 3801–3806 (1989). The growth factor was characterized as a heterodimer composed of subunits with molecular mass of 23 kDa. Leung et al. (Science 246: 1306–1309 [1989]), Keck et al. (Science 246: 1309–1312 [1989]) and Conn et al. (Proc. Natl. Acad. Sci USA 87: 2628–2632 [1990]) have described cDNAs which encode VEGF A which is homologous to the A and B chains of platelet-derived growth factor. Vascular endothelial growth factor I (VEGF I, VEGF AA) is a homodimer with an apparent molecular mass of 46 kDa, with each subunit having an apparent molecular mass of 23 kDa. VEGF I has distinct structural similarities to platelet-derived growth factor (PDGF), a mitogen for connective tissue cells but not vascular endothelial cells from large vessels.

OBJECTS OF THE INVENTION

It is, accordingly, an object of the present invention to provide novel vascular endothelial growth factor C subunit DNA free of other mammalian DNA. Another object is to provide recombinant genes capable of expressing VEGF C subunit subunit or dimer. Another object is to provide vectors containing the DNA sequences for VEGF A or B plus C subunits. A further object is to provide a host cell transformed with a vector containing the DNA sequence for VEGF A or B plus C or VEGF C alone. It is also an object to provide a recombinant process for making VEGF C subunit. Another object is to provide a novel vascular endothelial cell growth factor which contains the C subunit. This may include heterodimers AC and BC and homodimer CC.

SUMMARY OF THE INVENTION

Vascular endothelial cell growth factor C subunit DNA is prepared by polymerase chain reaction techniques. The DNA encodes a protein that may exist as either a heterodimer or homodimer. The protein is a mammalian vascular endothelial cell mitogen and as such is useful for the promotion of vascular development and repair. This unique growth factor is also useful in the promotion of tissue repair.

BRIEF DESCRIPTION OF THE DRAWING

FIGS. 1A–E. Full length amino acid residue protein translation product and its cDNA coding sequence for VEGF AA subunit A plus polypeptide cleavage products used to determine the amino acid sequence are shown in panels FIG. 1A through FIG. 1E (SEQ ID NOS:30 & 31).

FIGS. 2A–D. Full length amino acid residue protein translation product and its cDNA coding sequence for VEGF AB subunit A plus polypeptide cleavage products used to determine the amino acid sequence are shown in panels FIG. 2A through FIG. 2D (SEQ ID NOS:30 & 31).

FIGS. 3A–C. Full length amino acid residue protein translation product and its cDNA coding sequence for VEGF AB subunit B plus polypeptide cleavage products used to determine the amino acid sequence as shown in panels FIG. 3A through FIG. 3C (SEQ ID NOS:38 & 39).

FIG. 4. Full cDNA coding sequence and full length amino acid residue protein translation product for VEGF A 146 amino acid residue subunit SEQ ID NOS:32 & 33.

FIG. 5. Full cDNA coding sequence and full length amino acid residue protein translation product for VEGF A 190 amino acid residue subunit SEQ ID NOS:30 & 31.

FIGS. 6A–B. Full cDNA coding sequence and full length amino acid residue protein translation product for VEGF A 214 amino acid residue subunit SEQ ID NOS:34 & 35.

FIG. 7. Full cDNA coding sequence and full length amino acid residue protein translation product for VEGF B 138 amino acid residue subunit SEQ ID NOS:36 & 37.

FIG. 8. Full cDNA coding sequence and full length amino acid residue protein translation product for VEGF B 158 amino acid residue subunit SEQ ID NOS:38 & 39.

FIG. 9. Full cDNA coding sequence and full length amino acid residue protein translation product for VEGF C 154 amino acid residue subunit SEQ ID NOS:40 & 41.

FIG. 10. Full cDNA coding sequence and full length amino acid residue protein translation product for VEGF C 170 amino acid residue subunit SEQ ID NOS:44 & 45.

FIG. 11. Full cDNA coding sequence and full length amino acid residue protein translation product for VEGF C 149 amino acid residue subunit SEQ ID NOS:46 & 47.

FIG. 12. Full length amino acid and DNA sequence for human A215 is shown with/without arrows denoting alternative forms in panels 12A–B.

DETAILED DESCRIPTION

Figure 1A:
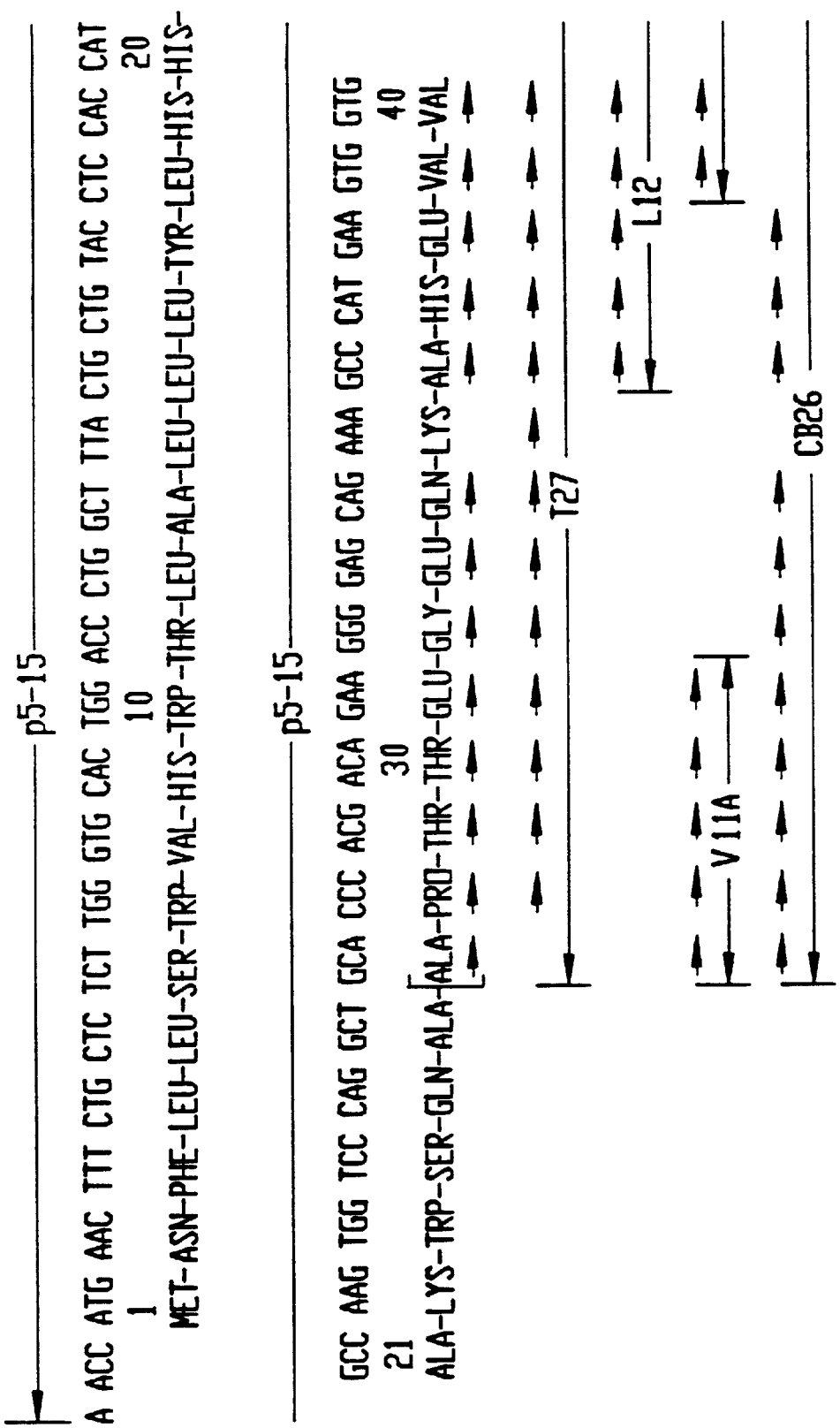
Figure 1B:
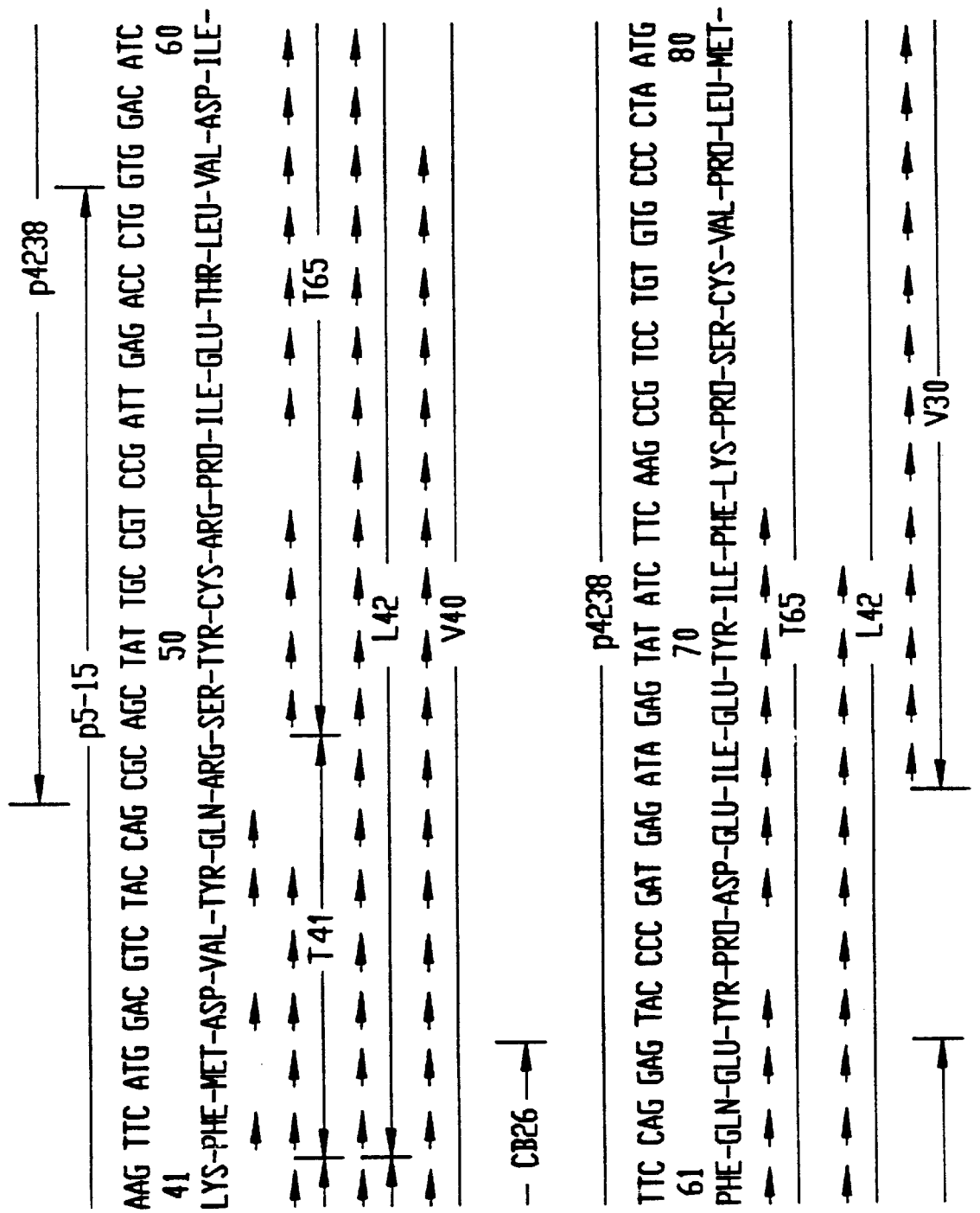
Figure 1D:
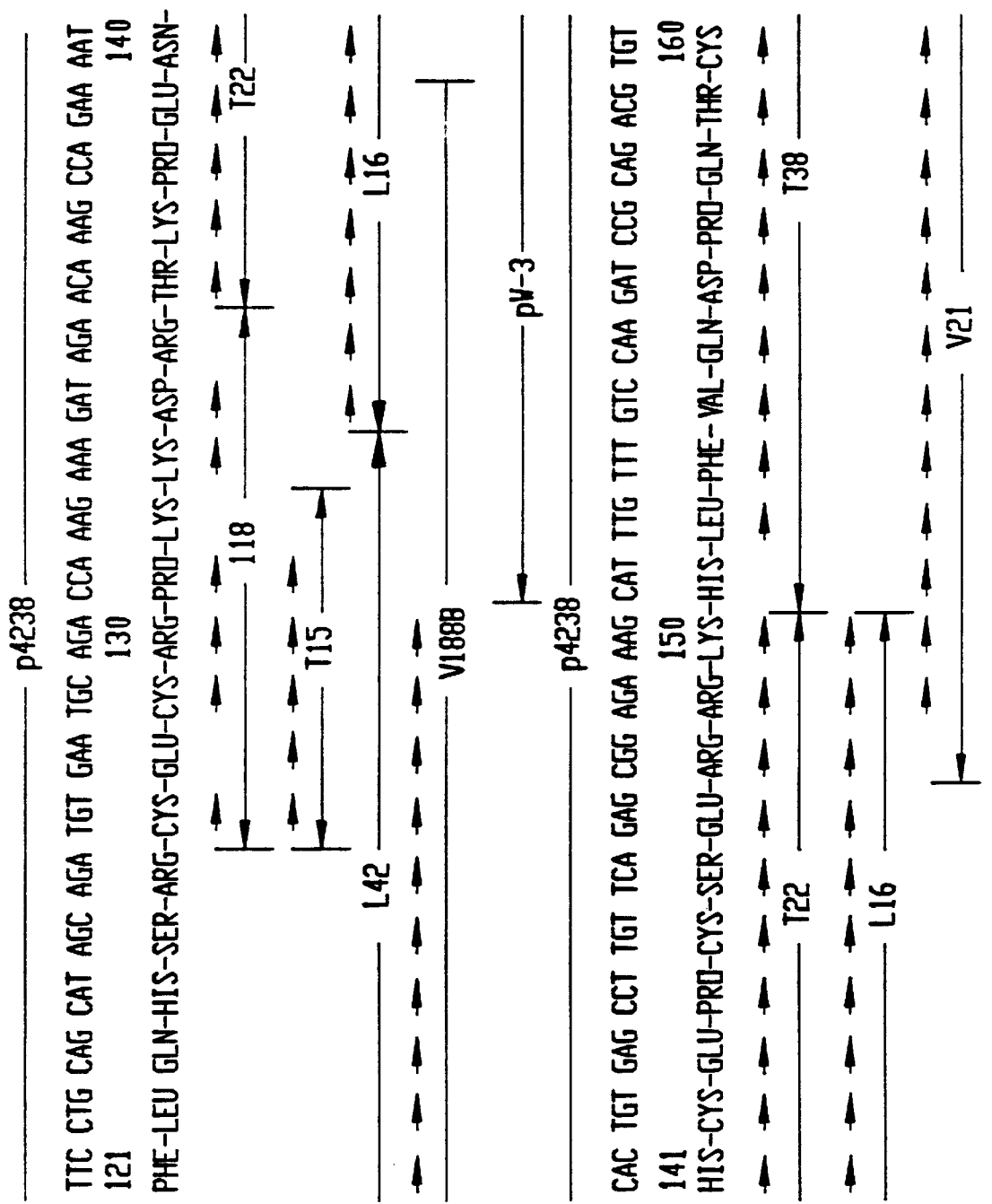
Figure 1E:
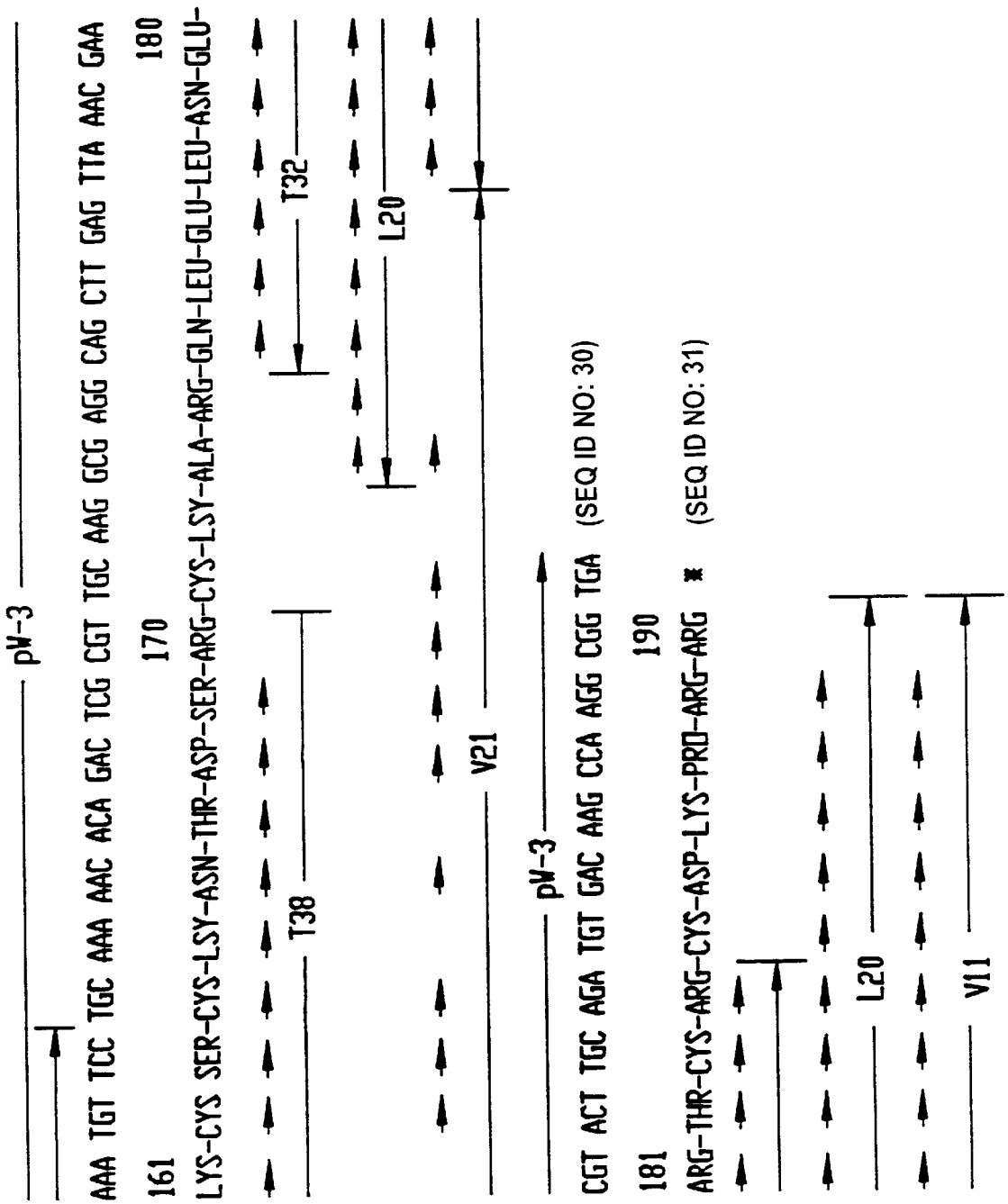
Figure 2A:
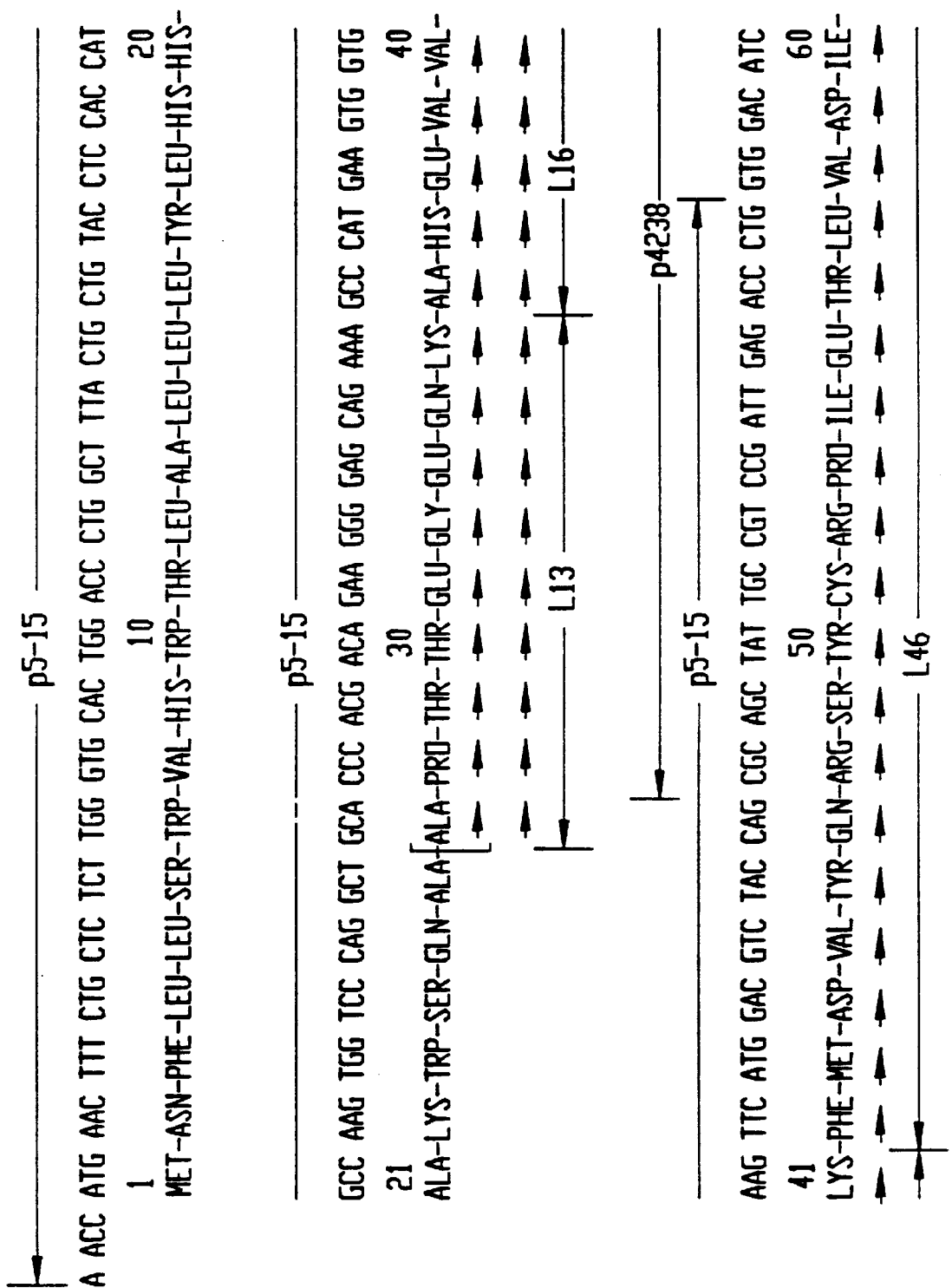

The present invention relates to a unique vascular endothelial cell growth factor (designated VEGF), isolated and purified from glioma cell conditioned medium, which exhibits mitogenic stimulation of vascular endothelial cells. Glioma is defined herein as any neoplasm derived from one of the various types of cells that form the interstitial tissue of the central nervous system including brain, spinal cord, posterior pituitary gland and retina. Consequently, the scope of the present invention is intended to include the unique growth factor isolated and purified from any mammalian tissue or other cells including cell lines. Cell lines include, but are not limited to, glioma-derived cell lines such as C6, hs 683 and GS-9L; glioblastomas such as A-172 and T98G; neuroblastomas such as IMR-32 and SK-N-MC; neurogliomas such as H4; tetromas such as XB-2; astrocytomas such as U-87 MG and U-373 MG; embryonal carcinomas and non-transformed glial or astrocyte cell lines, and the human medulloblastoma line TE 671, with GS-9L and TE 671 being preferred. VEGF AB is present and can be isolated from rat tissue including ovary, heart and kidney. Anterior pituitary tumor cell lines such as GH3 and Hs 199 may also be used. It is intended that VEGF of this invention can be obtained from any mammal species capable of producing VEGF, this includes, but is not limited to, rat and human.

Vascular endothelial cell growth factor may exist in various microheterogeneous forms which are isolated from one or more of the various cells or tissues described above. Microheterogeneous forms as used herein refer to a single gene product, that is a peptide produced from a single gene unit of DNA, which is structurally modified at the mRNA level or following translation. Peptide and protein are used interchangeably herein. The microheterogeneous forms will all have similar mitogenic activities. Biological activity and biologically active are used interchangeably and are herein defined as the ability of VEGF to stimulate DNA synthesis in target cells as described below which results in cell proliferation. The modifications may take place either in vivo or during the isolation and purification process. In vivo modification results from, but is not limited to, proteolysis, glycosylation, phosphorylation, deamidation or acetylation at the N-terminus. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which also results in production of microheterogeneous forms. The most common modification occurring during purification is proteolysis which is generally held to a minimum by the use of protease inhibitors. Under most conditions one or more microheterogeneous forms are present following purification of native VEGFs. Native VEGFs refers to VEGF isolated and purified from cells that produce VEGFs. Vascular endothelial cell growth factor may also exist in various alternatively spliced forms which is defined herein as the production of related mRNAs by differential processing of exons and introns. Exons are defined as those parts of the DNA sequence of a eukaryotic gene that code for the final protein product. It is also intended that the present invention includes VEGF subunits A,B and C which are defined as comprising the full length translation products of all alternatively spliced mRNAs made from the gene encoding the subunits and their corresponding mature amino acid sequences generated by proteolytic removal of the amino terminal secretory leader amino acid sequences. It is further intended that the invention only include those microheterogeneous and alternatively spliced VEGF subunits which when in the dimeric form exhibit biological activity as discussed below.

Glioma cells such as the rat cell line GS-9L are grown to confluence in tissue culture flasks, about 175 cm$^2$, in a cell culture medium such as Dulbecco's Modified Eagle's Medium (DMEM) supplemented with about 10% newborn calf serum (NCS). When the cells reach confluence the culture medium is removed, the cell layers are washed with Ca$^{++}$, Mg$^{++}$-free phosphate buffered saline (PBS) and are removed from the flasks by treatment with a solution of trypsin, about 0.1%, and EDTA, about 0.04%. The cells, about 1×10$^8$, are pelleted by centrifugation, resuspended in about 1500 ml of DMEM containing about 5% NCS and plated into a ten level cell factory (NUNC), 6,000 cm$^2$ surface area. The cells are incubated for about 48 to about 96 hours, with 72 hours preferred, at about 37° C. in an atmosphere of about 5% CO$_2$. Following incubation the medium is removed and the cell factories are washed about 3 times with PBS. About 1500 ml of fresh culture media is added containing about a 1:2 mixture of Ham's-F12/DMEM containing about 15 mM Hepes, pH about 7.4, about 5 μg/ml insulin, about 10 μg/ml transferrin and with or without about 1.0 mg/ml bovine serum albumin. This medium is replaced with fresh medium after about 24 hr and collected every 48 hr thereafter. The collected conditioned medium is filtered through Whatmen #1 paper to remove cell debris and stored at about −20° C.

The GS-9L conditioned medium is thawed and brought to pH 6.0 with 1 M HCl. The initial purification step consists of cation exchange chromatography using a variety of cation exchangers on a variety of matrices such as CM Sephadex C-50, Pharmacia Mono S, Zetachrom SP and Polyaspartic Acid WCX (Nest Group) with CM Sephadex C-50 (Pharmacia) being preferred. The VEGF-containing culture medium is mixed with CM Sephadex C-50 at about 2 gm per about 20 L of the conditioned medium and stirred at low speed for about 24 hr at 4° C. The resin is allowed to settle and the excess liquid is removed. The resin slurry is packed into a column and the remaining culture medium is removed. Unbound protein is washed from the column with 0.05 M sodium phosphate, about pH 6.0, containing 0.15 M NaCl. The VEGF AB is eluted with about 0.05 M sodium phosphate, about pH 6.0, containing about 0.6 M NaCl.

The active fractions collected from the CM Sephadex C-50 column are further fractionated by lectin affinity chromatography for additional purification of VEGF AB. The lectins which may bind VEGF AB include, but are not limited to, lectins which specifically bind mannose residues such as concanavalin A and lens culinaris agglutinin, lectins which bind N-acetylglucosamine such as wheat germ agglutinin, lectins that bind galactose or galactosamine and lectins which bind sialic acids, with concanavalin A (Con A) being preferred. A 0.9 cm diameter column containing about 5 ml packed volume of Con A agarose (Vector Laboratories) is washed and equilibrated with about 0.05 M sodium acetate, about pH 6.0, containing about 1 mM CaCl$_2$, about 1 mM MnCl$_2$ and about 0.6 M NaCl. The unbound protein is washed from the column with equilibration buffer. The VEGF AB is eluted with about 0.1 M NaCl buffer containing about 0.32 M α-methyl mannoside and about 0.28 M α-methyl glucoside.

The VEGF AB active eluate from the ConA column is applied to a Polyaspartic Acid WCX cation exchange high performance liquid chromatography (HPLC) column, 4.6 mm×250 mm, pre-equilibrated in about 0.05 M sodium phosphate buffer, pH 6.0. The column is eluted with a linear gradient of about 0 to 0.75 M NaCl in the phosphate buffer over about 60 minutes. The flow rate is maintained at about 0.75 ml/min collecting 0.75 ml fractions. Vascular endothelial cell growth factor AB activity is present in fractions eluting between approximately 21.7 and 28.5 ml.

The active fractions eluted from the polyaspartic WCX column that contain VEGF AB are pooled, adjusted to about pH 7.0 and loaded onto a 1×10 cm column of Pharmacia Chelating Sepharose 6B charged with an excess of copper chloride and equilibrated in about 0.05 M sodium phosphate, about pH 7.0, containing about 2 M NaCl and about 0.5 mM imidazole (A buffer). VEGF AB is eluted from the column with a gradient from 0–20% B over 10 minutes, 20–35% B over 45 minutes and 35–100% B over 5 minutes at a flow rate of 0.3 ml/min, where B buffer is 0.05 M sodium phosphate, pH 7.0, containing about 2 M NaCl and 100 mM imidazole. The active fractions containing VEGF AB activity eluted between about 12.6 and 22.8 ml of the gradient effluent volume.

The pooled fractions containing VEGF AB activity eluted from the metal chelate column are loaded onto a 4.6 mm×5 cm Vydac $C_4$ reverse phase HPLC column (5 µm particle size) previously equilibrated in solvent A [0.1% trifluoroacetic acid (TFA)]. The column is eluted with a linear gradient of about 0 to 30% solvent B over 15 minutes, 30% B for an additional 15 minutes, then 30–45% B over 22.5 minutes and finally 45–100% B over 5.5 minutes. Solvent B consists of solvent A containing 67% acetonitrile (v/v). The flow rate is maintained at about 0.75 ml/min and fractions are collected every minute. The homogeneous VEGF AB elutes from the C4 column under these conditions at between about 32 and about 38 ml of the gradient effluent volume.

Purity of the protein is determined by sodium dodecylsulfate (SDS) polyacrylamide gel electrophoresis (PAGE) in 12.5% crosslinked gels using the technique of Laemmli, Nature 227: 680–684 (1970). The silver stained gels show VEGF AB to consist of one band under non-reducing conditions with an approximate apparent molecular mass of about 58,000 daltons. When a sample containing the microheterogeneous forms of VEGF AB is separated under reducing conditions it migrates as two about 23 kilodalton (kDa) subunits. The purification process results in VEGF AB that is essentially free of other mammalian cell products, such as proteins. Recombinantly derived VEGF AB will also be free of mammalian cell products.

Biological activity is determined by mitogenic assay using mammalian vascular endothelial cells. Human umbilical vein endothelial (HUVE) cells are plated on gelatin-coated dishes at a density of about 5000 cells per well in about 500 µl of Medium 199 (M199) containing about 20% heat-inactivated fetal calf serum (FCS). Samples to be assayed are added at the time of plating. The tissue culture plates are incubated at about 37° C. for about 12 hours and about 2 microcuries of tritiated thymidine (NEN, 20 Ci/mmol) is added per ml of assay medium (1.0 µCi/well). The plates are incubated for a further 60 hr, the assay medium is removed and the plates are washed with Hanks balanced salt solution containing about 20 mM Hepes, about pH 7.5, and about 0.5 mg/ml bovine serum albumin. The cells are lysed and the labelled DNA solubilized with about 200 µl of a solution containing about 2 gm of sodium carbonate and about 400 mg sodium hydroxide in about 100 ml water. The incorporated radioactivity was determined by liquid scintillation counting. The concentration of VEGF which elicited a half-maximal mitogenic response in HUVE cells was approximately 2±1 ng/ml. The glycosaminoglycan heparin, which is required in these assays at a level of 10–100 µg/ml to promote a response to a positive control, acidic fibroblast growth factor, does not enhance mitogenic stimulation of these cells by VEGF AB.

A purified about 1–2 µg sample of VEGF AB is reduced in about 0.1 M Tris, about pH 9.5, with about 0.1% EDTA, about 6 M guanidinium chloride and about 20 mM dithiothreitol for about 2 hr at about 50° C. The reduced protein is carboxymethylated for about 1 hour in a solution containing about 9.2 µM of unlabelled and 2.8 µM of $^{14}$C-iodoacetic acid in about 0.7 M Tris, about pH 7.8, and about 0.1% EDTA and about 6 M guanidinium chloride. The protein is carboxymethylated for about 1 hr at room temperature. The protein is isolated after reduction and carboxymethylation by reverse phase HPLC chromatography on a Vydac $C_4$ column, about 4.6 mm×5 cm. The protein subunits are loaded onto a column pre-equilibrated with about 0.1% TFA and eluted by a 45 ml linear gradient from about 0.1% TFA to 0.1% TFA/67% acetonitrile at a flow rate of about 0.75 ml/min. The reduced and carboxymethylated protein eluted as two peaks at approximately 23 and 25 ml with the proportion being approximately equal as determined by monitoring absorbance at 210 nm.

Samples of the reduced and carboxymethylated subunits are applied to polybrene-coated glass fiber filters and their N-terminal sequences are determined by Edman degradation in an ABI gas phase microsequencer in conjunction with an ABI 120A on line phenylthiohydantoin analyzer following the manufacturers instructions. The protein showing the peak of absorbance eluting at approximately 25 ml (A subunit) yielded an amino terminal sequence of: SEQ ID NO:1

Ala Pro Thr Thr Glu Gly Glu Gln Lys Ala His Glu Val Val
which is identical to the A chain subunits of VEGF AA, Conn et al., Proc. Natl. Acad. Sci. USA 87: 2628–2632 (1990). The peak of absorbance eluting at approximately 23 ml (B subunit) yielded an N-terminal sequence of: SEQ ID NO:2

Ala Leu Ser Ala Gly Asn Xaa Ser Thr Glu Met Glu Val Val Pro Phe Asn Glu Val
plus a nearly equal amount of a truncated form of the same sequence missing the first three amino acid residues. The missing Xxx residue corresponds to an Asn residue in the cloned cDNA, see below. Since this missing Asn occurs in a classical Asn Xxx Ser/Thr N-glycosylation sequence it is presumed to be glycosylated. The A subunit and the total of both B subunits are recovered in nearly equal amounts supporting the interpretation that the two peptides combine to form an AB heterodimer in VEGF AB.

A sample of the A subunit was treated with either the protease trypsin which cleaves polypeptides on the C-terminal side of lysine and arginine residues or Lys C which cleaves polypeptides on the C-terminal side of lysine by procedures well known in the art. The peptides are isolated by reversed phase HPLC(RP-HPLC). The amino acid sequences of the isolated peptides are determined using the Edman degradation in the ABI gas phase sequenator in conjunction with the ABI 120 A on line phenylthiohydantoin analyzer following manufacturer's instructions. The amino acid sequences are shown in FIGS. 2A–D.

Reduced and carboxymethylated A subunit is dried and solubilized in about 0.7 M Tris, about pH 7.8, about 6 M guanidinium chloride containing about 0.1% EDTA. V8 protease is added in 0.1 M ammonium bicarbonate buffer, about pH 8.0, and the mixture is incubated for about 48 hr at about 37° C. The protease cleaves predominantly on the carboxyl terminal side of glutamic acid residues. The resulting polypeptides were resolved by $C_{18}$ RP-HPLC as above.

The reduced and carboxymethylated A subunit protein solution is adjusted to a pH of about 6.8 with 6 N HCl and dithiotreitol is added to a final concentration of 2 M for reduction of any methionine sulfoxide to methionine residues. After about 20 hr of reduction at about 39° C. the protein is repurified by $C_4$ HPLC. The product is dried and cleaved on the carboxyl terminal side of methionine residues by 200 μl of 40 mM cyanogen bromide in about 70% (v/v) formic acid under an argon atmosphere at about 20° C. for about 24 hr in the dark. The cleavage products are resolved by $C_{18}$ RP-HPLC. The amino acid sequence is shown in FIGS. 1A–E, see Conn et al., Proc. Natl. Acad. Sci USA 87: 2628–2632 (1990).

The full length 190 amino acid residue protein translation product of the VEGF AB, A subunit or subunit, which is now known to be identical with the VEGF AA, A subunit, and its cDNA coding sequence are shown in FIGS. 2A–D and 5. The mature amino terminus begins at residue 27, immediately following a typical hydrophobic secretory leader sequence. A single potential N-glycosylation site exists at $Asn_{100}$. Most (143 amino acid residues) of the 164 residues of the reduced and carboxymethylated mature subunit including the amino terminus and HPLC reversed phase-purified products of tryptic (T), Lys-C (L), *Staphylococcus aureus* V8 protease (V8) and cyanogen bromide (CB) cleavages, were determined by direct microsequencing (Applied Biosystems 470A) using a total of 5 μg of protein. All residues identified by amino acid sequencing are denoted by arrows pointing to the right either directly beneath the mature processed sequence following the bracket at residue 27 for the amino terminal determination of the whole subunit or, for residues identified from the polypeptide cleavage products, above the double-headed arrows spanning the length of the particular polypeptide. One listed pair of polypeptides, V18A and V18B, was sequenced as a mixture and, therefore, are only confirmatory of the cDNA-deduced amino acid sequence, see FIGS. 1 and 5.

Samples of the reduced and carboxymethylated pure VEGF AB, A and B subunits, were each digested with the Lys-C endoproteinase, which cleaves polypeptides on the C-terminal side of lysine residues. The peptides were isolated by reverse phase HPLC and their amino acid sequences were determined as described above. The locations of the peptides in the final VEGF AB, A and B sequences are shown in FIGS. 2A–D and FIGS. 3A–C, respectively.

The full length coding region of the A subunit is determined from three sets of overlapping cDNA clones. Degenerate oligonucleotide primers based on the amino acid sequences Phe-Met-Asp-Val-Tyr-Gln from polypeptide L42 (residues 42–47) and Cys-Lys-Asn-Thr-Asp from polypeptide T38 (residues 164–168) (see FIG. 1) were used to PCR amplify the central region of the cDNA for VEGF A chain following the procedure of Saiki et al., Science 230: 1350–1354 (1985). A single band migrating at 420 bp was gel purified, digested with SalI, ligated into pGEM3Zf(+) and sequenced. The nucleotide sequence obtained (p4238) was used to design antisense and sense PCR primers to amplify the 5' and 3' ends of the cDNA according to the protocol described by Frohman et al. Proc. Natl. Acad. Sci. USA 85: 8998–9002 (1988). These 5' and 3' clones are denoted p5-15 and pW3, respectively. Regions of complete DNA sequences, excluding the primers, determined for each set of clones are indicated by double-headed arrows above the nucleotide sequence. In addition to the cDNA coding the 190 amino acid form (164 amino acid secreted form identified by protein sequencing), two alternatively spliced cDNAs encoding a 146 amino acid and a 214 amino acid forms are cloned and sequenced, FIGS. 4, 5 and FIGS. 6A–B.

The full length coding region of the B subunit is determined from four sets of overlapping cDNA clones. Degenerate oligonucleotide primers based on the amino acid sequences from polypeptide L50 are used to PCR amplify the central region of the cDNA for VEGF AB, B subunit, following the procedure of Saiki et al., Science 230: 1350–1354 (1985). A single band migrating at 108 bp was gel purified, digested with SalI, ligated into pGEM3Zf(+) and sequenced. The nucleotide sequence obtained (pYG) was used to design antisense and sense PCR primers to amplify the 5' and 3' ends of the cDNA according to the protocol described by Frohman et al. Proc. Natl. Acad. Sci. USA 85: 8998–9002 (1988). These 5' and 3' clones are denoted p5V2 and p3V2, respectively. Additional 5' end sequences are determined from clone 202 isolated from a cDNA library prepared from GS-9L poly $A^+$ RNA. Regions of complete DNA sequences, excluding the primers, determined for each set of clones are indicated by double-headed arrows above the nucleotide sequence. The entire base sequence for the 158 amino acid microheterogeneous B subunit and the 138 amino acid microheterogeneous B subunit are shown in FIGS. 7 and 8.

The full length coding region of the C subunit is determined from three sets of overlapping cDNA clones. Degenerate oligonucleotide primers based on the amino acid sequence Phe Ser Pro Ser Cys Val and Glu Met Thr Phe Ser Gly from rat VEGF B subunit are used to PCR amplify the central region of the cDNA of VEGF C chain following the procedure of Saiki et al., Science 230: 1350–1354 (1985). A band migrating at 180 bp is gel purified, reamplified and digested with SalI, ligated into pGEM3Zf(+) and sequenced. The nucleotide sequence obtained (pFSEM') is used to design antisense and sense PCR primers to amplify the 5' and 3' ends of the cDNA according to the protocol described by Frohman et al., Proc. Natl. Acad. Sci. USA 85: 8998–9002 (1988). The 5' and 3' clones are denoted p5:16 and p3:19, respectively. The entire base sequence and amino acid sequence for this C subunit are shown in FIG. 9. The nucleotide sequence obtained from these overlapping cDNA clones was used to design antisense and sense PCR primers to amplify the full length coding region of the C subunit. The entire base sequence and amino acid sequence for the full length C subunit are shown in FIG. 10. In addition to the cDNA coding the 170 amino acid form, an alternatively spliced cDNA encoding a 149 amino acid form was cloned and sequenced, and is shown in FIG. 11.

It is intended that vascular endothelial cell growth factor of the present invention exist as a heterodimer consisting of an A microheterogeneous and/or alternatively spliced subunit consistent with a B microheterogeneous and/or alternatively spliced subunit or with a C microheterogeneous and/or alternatively spliced subunit. It is further intended that VEGF homodimer of the present invention exist as two C subunits. The native forms of the A, B, C subunits may be processed from alternatively spliced full length translation products. The heterodimers or heterodimeric species can be depicted as: A+B, A+C or B+C with the A, B or C subunits existing in any of the alternatively spliced or microheterogeneous forms. The homodimers or homodimeric species can be formed by combinations of any of the alternatively spliced or microheterogeneous forms. It is also intended that the invention include all of the individual subunit forms of the A subunit, the B subunit and the C subunit of VEGF.

It is further intended that the nucleotide sequence for vascular endothelial cell growth factor be interpreted to include all codons that code for the appropriate amino acids in the sequence for each of the vascular endothelial growth factor subunits, as indicated by the degeneracy of the genetic code. It is further intended that the nucleotide sequence and the amino acid sequence for VEGF subunits include truncated genes or proteins that result in proteins which exhibit biological activity similar to vascular endothelial cell growth factor. The scope of the invention is intended to include all naturally occurring mutations and allelic variants and any randomly generated artificial mutants which may change the sequences but do not alter biological activity as determined by the ability to stimulate the division of cells.

The above described heterodimers, homodimers and subunits of vascular endothelial cell growth factor are characterized by being the products of chemical synthetic procedures or of procaryotic or eucaryotic host expression of the DNA sequences as described herein. Expression of the recombinant VEGF genes (recombinant DNA) is accomplished by a number of different host cells which contain at least one of a number of expression vectors. Expression vectors are defined herein as DNA sequences that are required for the transcription of cloned copies of recombinant DNA sequences or genes and the translation of their mRNAs in an appropriate host. Such vectors can be used to express genes in a variety of hosts such as bacteria, blue-green algae, yeast cells, insect cells, plant cells and animal cells, with mammalian cells being preferred. The genes may also be expressed using any of a number of virus expression systems. Specifically designated vectors allow the shuttling of DNA between bacteria-yeast, bacteria-plant or bacteria-animal cells. An appropriately constructed expression vector should contain: an origin of replication for autonomous replication in host cells, selective markers, a limited number of useful restriction enzyme sites, a high copy number, strong promoters and efficient translational stop signals. A promoter is defined as a DNA sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses and cosmids. The expression of mammalian genes in cultured mammalian cells is well known in the art. Sambrook et al., Molecular Cloning, A Laboratory Manual, 2nd Edition, Book 3, Cold Springs Harbor Laboratory Press (1989) and Current Protocols In Molecular Biology, Ausubel et. al. Eds, Greene Publishing Associates and Wiley-Interscience, 1987 and supplements, disclose various mammalian expression vectors and vector systems along with methods for the introduction of recombinant vectors into mammalian cells. The cDNA for the A, B and C subunits can be expressed in a system such as that described by Linemeyer et al, European Patent Application, Publication No. 259,953. The cDNA is incorporated into a commercially available plasmid such as pKK 223-3 (Pharmacia) as modified as by Linemeyer et al. and expressed in $E.$ $coli$. Other expression systems and host cells are well known in the art.

The high Cys content and glycoslyation sites of the A, B and C subunits along with the structure of the homo- and heterodimers suggest that expression of biologically active proteins can be carried out in animal cells. Expression may be carried out in Chinese hamster ovary (CHO) cells with the cloned VEGF DNA cotransfected with the gene encoding dihydrofolate reductase (dhfr) into dhfr⁻CHO cells, see Sambrook et al. Transformants expressing dhfr are selected on media lacking nucleosides and are exposed to increasing concentrations of methotrexate. The dhfr and VEGF genes are thus coamplified leading to a stable cell line capable of expressing high levels of VEGF. The plasmid is designed to encode either an A subunit, a B subunit or a C subunit or a combination of any two of these subunits. The two cDNAs are present on the same plasmid and coexpressed allowing for the expression of heterodimers having VEGF biological activity. Plasmids containing a single subunit species may be used to cotransfect a suitable cell line.

The expressed proteins (homodimers or heterodimers) are isolated and purified by standard protein purification processes. It is to be understood that the expression vectors capable of expressing heterodimeric forms of VEGF will contain two DNA sequences which will encode either an A subunit and/or a DNA sequence which will encode a B subunit and/or a DNA sequence which will encode a C subunit. Expression vectors capable of expressing homodimeric forms of VEGF will contain either one or two DNA sequences which encode either A, B or C subunits.

The ability of the various species of VEGF to stimulate the division of cells such as vascular endothelial cells makes this protein in all microheterogeneous forms and alternative splicing forms useful as a pharmaceutical agent. The protein as used herein is intended to include all microheterogeneous forms as previously described. The protein can be used to treat wounds of mammals including humans by the administration of the novel protein to patients in need of such treatment.

The novel method for the stimulation of vascular endothelial cells comprises treating a sample of the desired vascular endothelial cells in a nutrient medium with mammalian VEGF, preferably human or rat, at a concentration of about 1–10 ng/ml. If the vascular endothelial cell growth is conducted in vitro, the process requires the presence of a nutrient medium such as DMEM or a modification thereof and a low concentration of calf or bovine serum such as about 0 to 2% by volume. Antibiotics may also be included; these are well known in the art.

The novel growth factors of this invention are useful for the coverage of artificial blood vessels with vascular endothelial cells. Vascular endothelial cells from the patient would be obtained by removal of a small segment of peripheral blood vessel or capillary-containing tissue and the desired cells would be grown in culture in the presence of VEGF and any other supplemental components that might be required for growth. After growth of adequate numbers of endothelial cells in culture to cover a synthetic polymeric blood vessel the cells would be plated on the inside surface of the vessel, such as fixed umbilical vein, which is then implanted in the patient. Alternatively, tubular supports are coated in vitro with VEGF prior to implantation into a patient. Following implantation endothelial cells migrate into and grow on the artificial surface. Prior coating of the artificial vessel either covalently or noncovalently, with proteins such as fibrin, collagen, fibronectin or laminin would be performed to enhance attachment of the cells to the artificial surface. The cell-lined artificial vessel would then be surgically implanted into the patient and, being lined with the patients own cells, would be immunologically compatible. The non-thrombogenic endothelial cell lining should decrease the incidence of clot formation on the surface of the artificial vessel and thereby decrease the tendency of vessel blockage or embolism elsewhere.

The novel proteins are also useful for the production of artificial vessels. Vascular endothelial cells and smooth muscle cells from the patient would be obtained and grown separately in culture. The endothelial cells would be grown in the presence of VEGF as outlined above. The smooth muscle would be grown in culture by procedures well known in the art. A tubular mesh matrix of a biocompatible polymer (either a synthetic polymer, with or without a coating of proteins, or a non-immunogenic biopolymeric material such as surgical suture thread) would be used to support the culture growth of the smooth muscle cells on the exterior side and vascular endothelial cells on the interior surface. Once the endothelial cells form a confluent monolayer on the inside surface and multiple layers of smooth muscle cells cover the outside, the vessel is implanted into the patient.

The novel peptides can also be used for the induction of tissue repair or growth. The pure VEGF would be used to induce and promote growth of tissue by inducing vascular growth and/or repair. The peptide can be used either topically for tissue repair or intravascularly for vascular repair. For applications involving neovascularization and healing of surface wounds the formulation would be applied directly at a rate of about 10 ng to about 1 mg/cm$^2$/day. For vascular repair VEGF is given intraveneously at a rate of about 1 ng to about 100 µg/kg/day of body weight. For internal vascular growth, the formulation would be released directly into the region to be neovascularized either from implanted slow release polymeric material or from slow release pumps or repeated injections. The release rate in either case is about 10 ng to about 100 µg/cm$^3$/day.

For non-topical application the VEGF is administrated in combination with pharmaceutically acceptable carriers or diluents such as, phosphate buffer, saline, phosphate buffered saline, Ringer's solution, and the like, in a pharmaceutical composition, according to standard pharmaceutical practice. For topical application, various pharmaceutical formulations are useful for the administration of the active compound of this invention. Such formulations include, but are not limited to, the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxy alkyl celluloses and alkylhydroxyalkyl celluloses, for example methylcellulose, hydroxyethyl cellulose, carboxymethyl cellulose, hydroxypropyl methylcellulose, and hydroxypropyl cellulose; polyoxamers such as Pluronic® Polyols exemplified by Pluronic® F-127; tetronics such as tetronic 1508; and alginates such as sodium alginate.

The following examples illustrate the present invention without, however, limiting the same thereto.

EXAMPLE 1
Preparation of Medium Conditioned By GS-9L Cells

GS-9L cells were grown to confluence in 175 cm$^2$ tissue culture flasks in Dulbecco's Modified Eagle's Medium/10% newborn calf serum (DMEM/NCS). At confluence the medium was decanted from the flasks, the flasks were washed with calcium and magnesium free phosphate buffered saline (PBS) and the cells were removed by treatment with a 1×solution of trypsin/EDTA (Gibco). The cells (1×10$^8$) were pelleted by centrifugation, resuspended in 1500 ml of DMEM/5% NCS and plated into a ten level (6000 cm$^2$ surface area) cell factory (NUNC). After 72 hours incubation at 37° C. in a 5% CO$_2$ atmosphere the medium was decanted and the cell factories were washed 3 times with PBS. The cells were refed with 1500 ml of a 1:2 mixture of Ham's F-12/DMEM containing 25 mM Hepes, pH 7.4, 5 µg/ml insulin, 10 µg/ml transferrin and 1.0 mg/ml bovine serum albumin. This medium was changed with fresh F-12/DMEM after 24 hours and collected every 48 hours after that. The conditioned medium was filtered through a Whatman #1 paper to remove cell debris and stored frozen at −20° C.

EXAMPLE 2
Carboxymethyl-Sephadex Chromatography of VEGF AA and VEGF AB

GS-9L conditioned medium, from Example 1, was thawed and brought to pH 6.0 with 1 M HCl. Two grams of CM Sephadex C-50 cation exchange (Pharmacia) resin pre-equilibrated in PBS adjusted to pH 6.0 with 1 N HCl were added to 20 liters of conditioned medium. The mixture was stirred at low speed for 24 hours at 4° C. The resin was then allowed to settle and the medium was siphoned off. The remaining resin slurry was packed into a 3.0 cm diameter column and any remaining medium was allowed to drain off. Unbound protein was washed off the column with 0.05 M sodium phosphate, pH 6.0, containing 0.15 M NaCl. Vascular endothelial growth factor activity was eluted from the column with a subsequent wash of 0.05 M sodium phosphate, pH 6.0, containing 0.6 M NaCl.

EXAMPLE 3
Concanavalin A (Con A) Lectin Affinity Chromatography of VEGF AA and VEGF AB A 0.9 cm diameter column containing about 5 ml of packed Con A agarose (Vector Laboratories) was equilibrated with 0.05 M sodium acetate, pH 6.0, containing 1 mM Ca$^{++}$, 1 mM Mn$^{++}$ and 0.6 M NaCl. The active eluate from the CM Sephadex C-50 column, Example 2, was applied to the Con A agarose and unbound protein was washed from the column with equilibration buffer. The column was then rinsed with three column volumes of 0.05 M sodium acetate, pH 6.0, containing 1 mM Ca$^{++}$, 1 mM Mn$^{++}$ and 0.1 M NaCl. Bound protein was subsequently eluted from the column by application of this buffer supplemented with 0.32 M α-methyl mannoside and 0.28 M α-methyl glucoside.

EXAMPLE 4
Polyaspartic Acid WCX HPLC Cation Exchange Chromatography of VEGF AA and VEGF AB The active eluate from the Con A column, Example 3, was applied to a 25 cm×4.6 mm poly(aspartic acid) WCX cation exchange HPLC column (Nest Group) pre-equilibrated in 0.05 M sodium phosphate buffer, pH 6.0. The column was eluted with a linear gradient of 0 to 0.75 M NaCl in this buffer over 60 minutes at a flow rate of 0.75 ml/min collecting 0.75 ml fractions. VEGF AB activity present in fractions eluting between approximately 21.7 and 28.5 ml were pooled.

EXAMPLE 5
Metal Chelate Chromatography

The active fractions eluted from the poly(aspartic acid) WCX column, Example 4, that contain VEGF AB were pooled, adjusted to pH 7.0 and loaded onto a 1×10 cm column of Pharmacia Chelating Sepharose 6B charged with an excess of copper chloride and equilibrated in 0.05 M sodium phosphate, pH 7.0, containing 2 M NaCl and 0.5 mM imidazole (A buffer). VEGF AB was eluted from the column with a gradient from 0–20% B over 10 minutes, 20–35% B over 45 minutes and 35–100% B over 5 minutes at a flow rate of 0.3 ml/min, where B buffer was 0.05 M sodium phosphate, pH 7.0, containing 2 M NaCl and 100 mM imidazole. The active fractions containing VEGF AB activity eluting between 12.6 and 22.8 ml of the gradient effluent volume were pooled.

EXAMPLE 6
Reverse Phase Chromatography

The fractions containing VEGF AB activity pooled from the metal chelate column, Example 5 were loaded onto a 4.6 mm×5 cm Vydac $C_4$ reverse phase HPLC column (5 μm particle size) equilibrated in solvent A (0.1% trifluoroacetic acid (TFA)). The column was eluted with a gradient of 0–30% solvent B over 15 minutes, 30% B for an additional 15 minutes, then 30–45% B over 22.5 minutes and finally 45–100% B over 5.5 minutes where solvent B = A containing 67% acetonitrile. The flow rate was maintained at 0.75 ml/min. The active VEGF AB fractions eluting between approximately 32.2 and 37.5 ml of the gradient effluent volume were pooled.

EXAMPLE 7

Mitogenic Assays

Human umbilical vein endothelial cells (HUVE) were plated on gelatin-coated 48 well tissue culture dishes at a density of 5000 cells/well in 500 μl of Medium 199 containing 20% heat inactivated fetal calf serum (FCS). Samples to be assayed were added at the time of plating. The tissue culture plates are incubated at 37° C. for 12 hours and 2 microcuries of tritiated thymidine (NEN, 20 Ci/mmol) was added per ml of assay medium (1.0 μCi/well). The plates were incubated for a further 60 hr, the assay medium was removed and the plates were washed with Hanks balanced salt solution containing 20 mM Hepes, pH 7.5, and 0.5 mg/ml bovine serum albumin. The cells were lysed and the labelled DNA solubilized with 200 μl of a solution containing 2 gm of sodium carbonate and 400 mg sodium hydroxide in 100 ml water. The incorporated radioactivity was determined by liquid scintillation counting.

The concentration of VEGF AB which elicited a half-maximal mitogenic response in HUVE cells was approximately 2±1 ng/ml. The glycosaminoglycan heparin, which is required in these assays at a level of 10–100 μg/ml to promote a response to a positive control, acidic fibroblast growth factor, does not enhance mitogenic stimulation of these cells by VEGF AB.

EXAMPLE 8

Purity And Protein Structural Characterization of VEGF AB

Purity of the protein under non-reducing conditions was determined by SDS-PAGE in 12.5% crosslinked gels according to the method of Laemmli, Nature 227: 680–685 (1970). The silver-stained gel contained a single band with an apparent mass of approximately 58 kDa. VEGF AB migrated in SDS-PAGE under reducing conditions in 15% crosslinked gels as a broad silver-stained band with apparent molecular mass of approximately 23 kDa.

VEGF AB was stored a 4° C. in the aqueous trifluoroacetic acid (TFA)/acetonitrile mixture used to elute the homogeneous protein in reversed phase $C_4$HPLC chromatography at the final stage of the purification protocol previously described. Aliquots of the purified protein (1–2 μg) were vacuum evaporated to dryness in acid-washed 10 ×75 mm glass tubes and reduced for 2 hours at 50° C. in 100 μl of 0.1 M Tris buffer, pH 9.5, and 6 M guanidinium chloride containing 0.1% EDTA and 20 mM dithiothreitol (Calbiochem, Ultrol grade) under an argon atmosphere. The reduced protein was subsequently carboxymethylated for 1 hour at 20° C. by the addition of 100 μl of 0.7 M Tris, pH 7.8, containing 0.1% EDTA, 6 M guanidinium chloride, 9.2 μM unlabeled iodoacetic acid and 50 μCi of iodo[2-$^{14}$C]acetic acid (17.9 mCi/mmole, Amersham). After completion of the carboxymethylation, the mixture was loaded directly onto a 4.6 mm×5.0 cm Vydac $C_4$ column which had been preequilibrated in 0.1% TFA. The reduced and carboxymethylated protein was repurified by elution with a 45 minute linear gradient of 0 to 67% (v/v) acetonitrile in 0.1% TFA at a flow rate of 0.75 ml/min and stored in this elution solution at 4° C. The reduced and carboxymethylated protein eluted as two peaks at approximately 23 and 25 ml that were of approximately equal area as determined by monitoring absorbance at 210 nm.

Samples of the two protein subunits isolated after reduction and carboxymethylation were each applied to polybrene-coated glass fiber filters and their N-terminal sequences were determined by Edman degradation in an ABI gas phase microsequencer in conjunction with an ABI 120A on line phenylthiohydantoin analyzer following manufacturers instructions. The peak of absorbance eluting at approximately 25 ml (A subunit) yielded an amino terminal sequence Ala Pro Thr Thr Glu Gly Glu Gln Lys Ala His Glu Val Val SEQ ID NO:1 identical to VEGF AA. The peak of absorbance eluting at approximately 23 ml (B subunit) yielded the N-terminal sequence Ala Leu Ser Ala Gly Asn Xaa Ser Thr Glu Met Glu Val Val Pro Phe Asn Glu Val SEQ ID NO:2 plus a nearly equal amount of a truncated form of the same sequence missing the first three residues. The missing X residue corresponds to an Asn in the cloned sequence. Since this missing Asn occurs in a classical Asn-X-Ser/Thr N-glycosylation sequence it is presumed to be glycosylated. The A and sum of the B chain peptides were recovered in nearly equal amounts supporting the interpretation that the two peptides combine to form an AB heterodimer in VEGF II.

Reduced and carboxymethylated A and B subunits (650 ng each) were each dried by vacuum evaporation in acid-washed 10×75 mm glass tubes. Lys C protease (50 ng, Boehringer Mannheim), an enzyme that cleaves on the carboxyl terminal side of lysine residues, was added to each tube in 100 μl of 25 mM Tris, pH 8.5, 0.1% EDTA. The substrate protein subunits were separately digested at 37° C. for 8 hours and the resulting polypeptides resolved by reversed phase HPLC chromatography on a 4.6 mm×25 cm Vydac $C_{18}$ column equilibrated in 0.1% TFA. Polypeptides were fractionated by elution with a 2 hour linear gradient of 0–67% acetonitrile in 0.1% TFA at a flow rate of 0.75 ml/min at 20° C. Individual peaks were manually collected and stored in this elution solution at 4° C.

The amino acid sequences of the isolated peptides were then determined using Edman degradation in an ABI gas phase sequenator in conjunction with the ABI 120 A on line phenylthiohydantoin analyzer (Applied Biosystems Int.). The peptide sequences are shown in the following FIGS. 2 and 3. The amino acid sequence of Lys C fragment L20 (FIG. 5) demonstrates that the form of VEGF AB mature A subunit in the heterodimer is the 164 amino acid form. The amino acid sequence of Lys C fragment L26 (FIGS. 3A–C) demonstrates that the form of VEGF AB mature B subunit in the heterodimer is the 135 amino acid form derived from the 158 full length amino acid form.

EXAMPLE 9

Cloning and Sequencing of the VEGF A Subunit

PCR Amplification, Cloning and Sequencing of P4238

Two degenerate oligonucleotides were synthesized in order to amplify the cDNA encoding the peptide sequences of VEGF A subunit between Lys C fragment L 42 and tryptic fragment T38. These oligonucleotides were:

L42.2 5' TTTGTCGACTT[TC]ATGGA[TC]GT[N]TA[TC]CA 3'    SEQ ID NO:3

T383'B
5' CAGAGAATTCGTCGACA[AG]TC[N]GT[AG]TT[TC]TT
[AG]CA 3'    SEQ ID NO:4 where N=ACGT

Poly A⁺ RNA was isolated from GS-9L cells using the Fast Track RNA isolation kit from Invitrogen and the protocol provided. First strand cDNA synthesis was performed as follows;

1 μg of GS-9L RNA was annealled to 1 μg of adapter primer TA17, 5' GACTCGAGTCGACATC-GATTTTTTTTTTTTTTTTT 3' SEQ ID NO:5, by incubating in a volume of 10 μl at 70° C. for 5 min. followed by cooling to room temperature. To this reaction was added:

3.0 μl water
2.5 μl 10×buffer (500 mM Tris-HCl pH 8.3, 750 mM KCl, 100 mM MgCl$_2$, 5 mM spermidine)
2.5 μl 100 mM DTT
2.5 μl 10 mM each dATP, dGTP, dCTP, dTTP
0.6 μl 15 units RNasin
2.5 μl 40 mM Na pyrophosphate
1.5 μl 15 units reverse transcriptase and the reaction was incubated at 42° C. for 1 hour, then diluted to 1 ml in 10 mM Tris-HCl mM EDTA, pH 7.5.

PCR Reactions:
Primary reaction (100 μl)
10 μl 10×buffer from Perkin Elmer Cetus GeneAmp kit
16 μl 1.25 mM each stock of dATP, dCTP, dGTP, and dTTP
2 μl first strand GS9L cDNA
2 μl 50 pMoles L42.2
2 μl 50 pMoles T383'B
0.5 μl 2.5 units Amplitaq DNA polymerase
67.5 μl water
Reaction conditions, 40 cycles of 94° C., 1'; 50° C., 2'30"; 72° C., 2'.

Prep scale secondary reaction:
100 μl 10×buffer
160 μl 1.25 mM each stock of dATP, dCTP, dGTP, and dTTP
10 μl primary PCR reaction
20 μl 500 pMoles L42.2
20 μl 500 pMoles T383'B
5 μl 25 units Amplitaq DNA polymerase
685 μl water
Reaction conditions 94° C., 1'; 55° C., 2'; 72° C., 2'; 30 cycles.

The PCR product was concentrated by Centricon 30 spin columns, purified on a 1% agarose gel, and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method.

PCR Amplification, Cloning and Sequencing of pW-3

Based on the sequence obtained from the p4238 clones, two specific PCR primers were synthesized; oligo 307 5' TTTGTCGACTCAGAGCGGAGAAAGC 3' SEQ ID NO:6 and oligo 289 5' TTTGTCGACGAAAATCACTGTGAGC 3' SEQ ID NO:7. These primers were used in combination with oligoA 17 5' GACTCGAGTCGACATCG 3' SEQ ID NO:8 to amplify the cDNA encoding the COOH terminus of VEGF A subunit using the 3' RACE technique described by Frohman et al., PNAS 85: 8998–9002 (1988).

PCR reactions:
Primary reaction 100 μl
10 μl 10×buffer from Perkin Elmer Cetus GeneAmp kit
18 μl 1.25 mM each stock of dATP, dCTP, dGTP, and dTTP
0.35 μl first strand GS-9L cDNA
2 μl 50 pMoles oligo 289
0.5 μl 2.5 units Amplitaq DNA polymerase
67.15 μl water
Reaction conditions 94° C., 1'; 58° C., 2'; 72° C., 2'; 10 cycles then add 50 pMoles A17, then 1 cycle of 94° C., 1'; 58° C., 2'; 72° C., 40' followed by 40 cycles 94° C., 1'; 58° C., 2'; 72° C., 2'.

Prep Scale secondary reaction:
60 μl 10×buffer
108 μl 1.25 mM each stock of dATP, dCTP, dGTP, and dTTP
24 μl primary PCR reaction
12 μl 300 pMoles oligo 307
12 μl 300 pMoles oligo A17
3 μl 15 units Amplitaq DNA polymerase 381 μl water
Reaction conditions 94° C., 1'; 58° C., 2'; 72° C., 2'; 30 cycles.

The PCR product was purified on a 1% agarose gel and digested with restriction endonuclease SalI. The SalI fragment was then ligated into SalI cut pGEM3Zf(+). The ligation mix was used to transform *E. coli* XL-1 blue. Plasmid DNA was isolated from white transformants and sequenced by the dideoxy chain termination method.

PCR Amplification, Cloning and Sequencing of p5-15

Based on the sequence of p4238 clones, two specific PCR primers were synthesized; oligo 113 5' TTTGTCGACAA-CACAGGACGGCTTGAAG 3' SEQ ID NO:9 and oligo 74 5' TTTGTCGACATACTCCTGGAAGATGTCC 3' SEQ ID NO:10. These primers were used in combination with oligo A17 5' GACTCGAGTCGACATCG 3' SEQ ID NO:8 to amplify the cDNA encoding the amino terminus of VEGF A subunit using the 5' RACE technique described by Frohman et al., supra. Oligo 151 was synthesized in order to specifically prime VEGF A subunit cDNA from GS-9L RNA. Oligo 151 is 5' CTTCATCATTGCAGCAGC 3' SEQ ID NO:11.

RNA was isolated from GS-9L cells using the Fast Track RNA isolation kit from Invitrogen using the protocol provided. First strand cDNA synthesis was performed as follows;

One μg of GS9L RNA was annealled to 1 μg of oligo 151 by incubating in a volume of 6 μl at 70° C. for 5' followed by cooling to room temperature. To this reaction was added:
1.5 μl 10×buffer (500 mM Tris-HCl, pH 8.3,
750 mM KCl, 100 mM MgCl$_2$, 5 mM spermidine)
2.5 μl 10 DTT
2.5 μl 10 mM each dATP, dGTP, dCTP, dTTP
0.6 μl 25 units RNasin
2.5 μl 40 mM Na pyrophosphate
9.5 μl 20 units diluted reverse transcriptase The reaction was incubated at 42° C. for 1 hour. Excess oligo 151 was removed by Centricon 100 spin columns and the 5' end of the cDNA was tailed by the addition of dATP and terminal transferase. The tailed cDNA was diluted to a final volume of 150 μl in 10 mM Tris-HCl, 1 mM EDTA, pH 7.5.

PCR Reactions:
Primary reaction (50 μl)
5 μl 10×buffer from Perkin Elmer Cetus GeneAmp Kit
8 μl 1.25 mM each stock of dATP,dCTP,dGTP, and dTTP
5 μl first strand GS-9L cDNA prime with oligo 151 and tailed
1 μl 25 pMoles oligo 113
1 μl 25 pMoles oligo A17
1 μl 10 pMoles oligo TA17
0.25 μl 1.25 units Amplitq DNA polymersase
28.75 μl water
Reaction conditions; 1 cycle 94° C. 1'; 50° C. 2'; 72° C. 40' then 40 cycles of 94° C. 1'; 50° C. 1'30"; 72° C. 2'
Prep scale secondary reaction:
60 μl 10×buffer
96 μl 1.25 mM each stock of dATP, dCTP, dGTP, and dTTP
6 μl primary PCR reaction
12 μl 300 pMoles oligo74
12 μl 300 pMoles oligo A17
3 μl 15 units Amplitaq DNA polymerase
411 μl water
Reaction conditions 94° C., 1'; 55° C., 2'; 72° C., 2' 30 cycles.

The PCR product was concentrated by Centricon 100 spin columns, and digested with restriction endonuclease SalI. The SalI fragment was then ligated into SalI cut pGEM3Zf (+). The ligation mix was used to transform *E. coli* XL-1 blue. Plasmid DNA was isolated from white transformants and sequenced by the dideoxy chain termination method. The base sequence is shown in FIG. 5.
Cloning and sequencing of alternative forms of VEGF A cDNA Based on the sequence obtained from the p5-15 and pW-3 clones, two specific PCR primers were synthesized; oligo 5'C. 5' TTTGTCGACAACCATGAACTTTCTGC 3' SEQ ID NO:12 and oligo 181 5' TTTGTCGACGGTGAGAG-GTCTAGTTC 3' SEQ ID NO:13. These primers were used together to amplify multiple cDNAs encoding alternative forms of the VEGF A subunit.
Preparative PCR Reaction:
50 μl 10×buffer
80 μl 1.25 mM each stock of dATP, dCTP, dGTP, and dTTP
10 μl first strand GS-9L cDNA
10 μl 300 pMoles oligo 5'C
10 μl 300 pMoles oligo 181
2.5 μl 15 units Amplitaq DNA polymerase
337.5 μl water
Reaction conditions 94° C., 1'; 58° C., 2'; 72° C., 3'; 40 cycles.

The PCR product was extracted with phenol/chloroform, concentrated by Centricon 30 spin columns, precipitated by ethanol, and digested with restriction endonuclease SalI, and ligated into SalI cut pGEM3Zf(+). The ligation mix was used to transform *E. coli* XL-1 blue. Plasmid DNA was isolated from white transformants and sequenced by the dideoxy chain termination method. Three sets of clones were identified. Clone #12 encoded the 190 amino acid form of VEGF A subunit identical to that shown in FIG. 1. The 164 amino acid secreted form of VEGF A subunit is that amino acid sequence running continuously from $Ala^{27}$ to $Arg^{190}$. Clone#14 has a 135 base pair deletion between the second base of the $Asn^{140}$ codon and the third base of the $Arg^{184}$ codon. This clone thus encodes a 146 aa form of the VEGF A subunit with the conversion of $Asn^{140}$ to $Lys^{140}$. The 120 amino acid secreted form of VEGF A subunit runs from $Ala^{27}$ to $Asn^{140}$, which becomes $Lys^{140}$ and does not begin until $Cys^{185}$, this form also finishes at $Arg^{190}$, FIG. 4. Clone #16 has a 72 base pair insertion between the second and third base of the $Asn^{140}$ codon. This clone thus encodes the 214 amino acid form of the VEGF A subunit with the conversion of $Asn^{140}$ to $Lys^{140}$, FIG. 6.

EXAMPLE 10

Cloning and Sequencing of the VEGF B Subunit

PCR Amplification, Cloning and Sequencing of pYG

Two degenerate oligonucleotides were synthesized in order to amplify the cDNA encoding the peptide sequences of VEGF B on Lys C fragment L50. These oligonucleotides were:

YI 5' TTTGTCGACATA[TC]AT[TCA]GC[N]GA[TC]GA[AG]C 3'     SEQ ID NO:14

GC 5' TTTGTCGACTC[AG]TC[AG]TT[AG]CA[AG]CA[N]CC 3'
SEQ ID NO:15 where N = ACGT

RNA was isolated from GS-9L cells using the Fast Track RNA isolation kit from Invitrogen and the protocol provided. First strand cDNA synthesis was performed as follows;

1 μg of GS-9L poly $A^+$RNA was annealled to 1 μg of adapter primer TA17, 5'GACTCGAGTCGACATC-GATTTTTTTTTTTTTTTTT 3' SEQ ID NO: 5, by incubating in a volume of 10 μl at 70° C. for 5 min. followed by cooling to room temperature. To this reaction was added:
3.0 μl water
2.5 μl 10×buffer (500 mM Tris-HCl, pH 8.3, 750 mM KCl, 100 mM $MgCl_2$, 5 mM spermidine)
2.5 μl 100 mM DTT
2.5 μl 10 mM each dATP, dGTP, dCTP, dTTP
0.6 μl 15 units RNasin
2.5 μl 40 mM Na pyrophosphate
1.5 μl 15 units reverse transcriptase
and the reaction was incubated at 42° C. for 1 hour, then diluted to 1 ml in 10 mM Tris-HCl, 1 mM EDTA, pH 7.5.
PCR Reactions:
Primary reaction (50 μl)
5 μl 10×buffer from Perkin Elmer Cetus GeneAmp kit
8 μl 1.25 mM each stock of dATP, dCTP, dGTP, and dTTP
1 μl first strand GS-9L cDNA
1 μl 50 pMoles oligo YI
1 μl 50 pMoles oligo GC
0.25 μl 1.25 units Amplitaq DNA polymerase
33.75 μl water
Reaction conditions, 40 cycles of 94° C., 1'; 50° C., 2'; 72° C., 2'.
Prep scale reaction:
60 μl 10×buffer
96 μl 1.25 mM each stock of dATP, dCTP, dGTP, and dTTP
12 μl first strand 659L cDNA
12 μl 500 pMoles oligo YI 12 µl 500 pMoles oligo GC
3 µl 15 units Amplitaq DNA polymerase
405 µl water
Reaction conditions 94° C., 1'; 50° C., 2'; 72° C., 2' 40 cycles.

The PCR product was concentrated by Centricon 30 spin columns and digested with restriction endonuclease SalI. The SalI fragment was then ligated into SalI cut pGEM3Zf (+). The ligation mix was used to transform E. coli XL-1 blue. Plasmid DNA was isolated from white transformants and sequenced by the dideoxy chain termination method.

PCR Amplification, Cloning and Sequencing of p3V2

Based on the sequence obtained from the pYG clones, a specific PCR primer was synthesized; oligo HP 5' TTTGTCGACACACCCTAATGAAGTGTC 3' SEQ ID NO:16. This primer was used in combination with oligo A17 5' GACTCGAGTCGACATCG 3' SEQ ID NO:8 to amplify the cDNA encoding the COOH terminus of the VEGF B subunit using the 3' RACE technique described by Frohman et al., PNAS 85: 8998–9002 (1988).

Preparative PCR reaction:
60 µl 10×buffer from Perkin Elmer Cetus Gene Amp Kit
12 µl first strand 659L cDNA
96 µl 1.25 mM each of dATP, dCTP, dGTP, dTTP
12 µl 300 pMoles oligo A17
12 µl 300 pMoles oligo HP
3 µl 15 units Amplitaq DNA polymerase
405 µl water
Reaction conditions 1 cycle of 94° C., 1'; 58° C., 2'; 72° C., 2'; followed by 40 cycles 94° C., 1', 58° C., 2' and 72° C., 2'.

The PCR product was concentrated by Centricon 30 spin columns, precipitated with ethanol and digested with restriction endonuclease SalI. The SalI fragment was then ligated into SalI cut pGEM3Zf(+). The ligation mix was used to transform E. coli XL-1 blue. Plasmid DNA was isolated from white transformants and sequenced by the dideoxy chain termination method.

PCR Amplification, Cloning and Sequencing of p5V2

Based on the sequence of pYG clones, two specific PCR primers were synthesized; oligoVL' 5' TTTGTCGACAACAGCGACTCAGAAGG 3' SEQ ID NO: 17 and oligoVS' 5' TTTGTCGACACTGAATATATGAGACAC 3' SEQ ID NO:18. These primers were used in combination with oligo A17 5' GACTCGAGTCGACATCG 3' SEQ ID NO:8 to amplify the cDNA encoding the amino terminus of the VEGF B subunit using the 5' RACE technique described by Frohman et al., supra. Oligo 151 was synthesized in order to prime cDNA from GS-9L RNA. Oligo 151 is 5' CTTCATCATTGCAGCAGC 3' SEQ ID NO: 11.

Poly A⁺RNA was isolated from GS9L cells using the Fast Track RNA isolation kit from Invitrogen using the protocol provided. First strand cDNA synthesis was performed as follows:

One µg of GS9L RNA was annealled to 1 µg of oligo151 by incubating in a volume of 6 µg at 70° C. for 5' followed by cooling to room temperature. To this reaction was added:
1.5 µl 10×buffer (500 mM Tris-HCl, pH 8.3, 750 mM KCl, 100 mM MgCl₂, 5 mM spermidine)
2.5 µl 10 mM DTT
2.5 µl 10 mM each dATP, dGTP, dCTP, dTTP
0.6 µl 25 units RNasin
2.5 µl 40 mM Na pyrophosphate
9.5 µl 20 units diluted reverse transcriptase
The reaction was incubated at 42° C. for 1 hour.

Excess oligo 151 was removed by Centricon 100 spin columns and the 5' end of the cDNA was tailed by the addition of dATP and terminal transferase. The tailed cDNA was diluted to a final volume of 150 µl in 10 mM Tris-HCl, 1 mM EDTA, pH 7.5

PCR Reactions:
Primary reaction (50 µl)
5 µl 10×buffer from Perkin Elmer Cetus GeneAmp Kit
8 µl 1.25 mM each stock of dATP,dCTP,dGTP, and dTTP
5 µl first strand GS9L cDNA primed with oligo151 and tailed
1 µl 25 pMoles oligo VL'
1 µl 25 pMoles oligo A17
1 µl 10 pMoles oligo TA17
0.25 µl 1.25 units Amplitq DNA polymersase 28.75 µl water
Reaction conditions; 1 cycle 94° C., 1'; 58° C., 2'; 72° C., 40' then 40 cycles of 94° C., 1'; 58° C., 2'; 72° C., 2'.

Prep scale secondary reaction:
100 µl 10×buffer
160 µl 1.25 mM each stock of dATP, dCTP, dGTP, and dTTP
10 µl primary PCR reaction
20 µl 500 pMoles oligo VS'
20 µl 300 pMoles oligo A17
5 µl 25 units Amplitaq DNA polymerase
685 µl water
Reaction conditions 94° C., 1'; 58° C., 2'; 72° C., 2' 30 cycles.

The PCR product was extracted with phenol/chloroform, concentrated by Centricon 30 spin columns, precipitated by ethanol, and digested with restriction endonuclease SalI. The SalI fragment was purified on 4% Nu-Sieve Agarose gel then ligated into SalI cut pGEM3Zf(+). The ligation mix was used to transform E. coli XL-1 blue. Plasmid DNA was isolated from white transformants and sequenced by the dideoxy chain termination method.

PCR Amplification, Cloning and Sequencing of pCV2 And pCV2.1

Based on the sequences of the p3V2 and p5CV2 clones, two specific PCR primers were synthesized; oligo 5'CV2.1 5' TTTGTCGAC[N][N]GCAGGTCCTAGCTG 3' SEQ ID NO;19 and oligo 3'CV2 5' TTTGTCGAC[N][N]CTAATAAATAGAGGG 3' SEQ ID NO:20. These primers were used together to amplify the cDNA encoding the VEGF B subunit.

Preparative PCR Reaction:
40 µl 10×buffer
64 µl 1.25 mM each dATP, dTTP, dGTP, dCTP
8 µl first strand GS-9L cDNA
8 µl 200 pMoles 5'CV2.1
8 µl 200 pMoles 3'CV2
2 µl 10 units Amplitaq DNA polymerase
270 µl water
Reaction conditions: 94° C., 1', 58° C., 2', 72° C., 2'; 40 cycles.

The PCR product was extracted with phenol/chloroform, concentrated by Centricon 30 spin columns, precipitated by ethanol, and digested with restriction endonuclease Sal I, and ligated into Sal I cut pGEM3Zf(+). The ligation mix was used to transform E. coli XL-1 blue. Plasmid DNA was isolated form white transformants and sequenced by the dideoxy chain termination method. Two sets of clones were identified, one encoded a 158 amino acid sequence and the other encoded a 138 amino acid sequence, see FIGS. 3, 7 and 8.

cDNA Cloning of VEGF B Subunit

The DNA and protein sequences for the amino terminus of the signal peptide of VEGF B was determined from a cDNA clone isolated from a cDNA library constructed from GS-9L polyA+RNA.

First Strand Synthesis

Anneal 15.6 μl (5 ug) GS-9L polyA+ RNA and 2.5 μl (2.5 ug) oligo dT-XbaI primer by heating to 70° C. 5' slow cool to room temperature. Add the following:
5.5 μl 10×buffer (500 mM Tris-HCl, pH 8.3, 42° C.), 750 mM KCl, 100 mM $MgCl_2$, 5 mM spermidine
5.5 μl 100 mM DTT
5.5 μl 10 mM each dATP, dTTP, dCTP, dGTP
1.4 μl (55 units) RNasin
5.5 μl 40 mM NaPPi
13.5 μl 55 units AMV reverse transcriptase
Incubate at 42° C. 60'.

Second Strand Synthesis:

Assemble reaction mix
50 μl first strand reaction
25 μl 10×buffer (500 mM Tris-HCl, pH 7.2, 850 mM KCL, 30 mM $MgCl_2$ 1 mg/ml BSA, 100 mM $(NH_4)_2SO_4$
7.5 μl 100 mM DTT
25 μl 1 mM NAD
6.5 μl (65 units) E. coli DNA PolymeraseI
2.5 μl (2.5 units) E. coli DNA Ligase
2.5 μl (2 units) E. coli RNase H
135 μl water
Incubate at 14° C. for 2 h and then incubate 70° C. for 10'. Add 1 ul (10 units) T4 DNA Polymerase, incubate at 37° C. for 10', add 25 μl 0.2M EDTA an extract with phenol/chloroform, then precipitate by the addition of 0.5 volume of 7.5 M ammonium acetate and 3 volumes of ethanol, collect precipitate and resuspend in 20 μl of 10 mM Tris-HCl, pH 7.5, 1 mM EDTA.

cDNA Library Construction

The above cDNA was ligated into EcoR1/XbaI digested LambdaGEM-4 (Promega Biochemicals) after the addition of EcoR1 linkers and digestion with EcoR1 and XbaI. A cDNA library was amplified from ~50,000 independent clones.

Isolation of Rat VEGF B cDNA Clone

The above cDNA library was screened by placque hybridization using pCV2 as a probe. Hybridization conditions were as follows:

5×SSC (1×SSC is 0.15M sodium chloride, 0.015M sodium citrate),
50% Formamide
5×Denhardt's Solution (1% Ficoll, 1% polyvinylpyrrolidone, 1% bovine serum albumin)
0.15 mg/ml salmon sperm DNA
hybridize overnight at 42° C.

Filters were washed 3 times in 2×SSC, 0.1% SDS at room temperature for 5', then 1 time in 1×SSC, 0.1% SDS at 50° C. for 30'. Positive clones were identified by autoradiography.

The DNA from phage #202 (FIG. 3) was digested with restriction endonuclease SpeI and the 1.1 kb band ligated into XbaI digested pGEM3Zf(+). The ligation mix was used to transform E.coli XL-1 blue. Plasmid DNA was isolated from white transformants and sequenced by the dideoxy chain termination method. The cDNA sequence and predicted amino acid sequence of the signal peptide are shown in FIGS. 7 and 8.

The entire nucleotide and amino acid sequence of the 138 amino acid form is shown in FIG. 7. The secreted protein starts at $Ala^{24}$ and continues to $Arg^{38}$. The entire nucleotide and amino acid sequence of the 158 amino acid form is shown in FIGS. 8. The secreted protein starts at $Ala^{24}$ and continues to $Leu^{158}$.

EXAMPLE 11

Cloning and sequencing VEGF C Subunit
PCR Amplification, Cloning and Sequencing of pFSEM'

Two degenerate oligonucleotides were synthesized based on the sequence of rat VEGF B subunit in order to amplify VEGF cDNAs from the human medulloblastoma line TE-671, ATCC HTB (McAllister et al., Int. J. Cancer 20: 206–212 [1977]). These oligonucleotides were:

```
FS 5' TTTGTCGACA TTC AGT CC(N) TC(N) TG(TC) GT 3'   SEQ ID NO:21

EM' 5' TTTGTCGACA CTG AGA GAA (N)GT CAT (CT)TC 3'
SEQ ID NO:22
where N = AGCT
```

Poly $A^+$RNA was isolated from TE-671 cells using the Fast Track RNA isolation kit from Invitrogen and the protocol provided. First strand cDNA synthesis was performed as follows using the cDNA Cycle kit from Invitrogen;

1 μl 1 μg of TE-671 polyA+ RNA
19 μl water
5 μl 100 mM MeMgOH
6.25 μl 0.7M B-mercaptoethanol
2.5 μl random primer
2.5 μl RNase Inhibitor
10 μl 5×RT buffer
2.5 μl 25 mM dNTPs
1.25 μl reverse transcriptase 12.5 units The reaction was incubated for 60' at 42° C., then 3' at 95° C., placed on ice, then an additional 1.25 ul reverse transcriptase was added and the reaction incubated an additional 60' at 42° C.

The above procedure was performed in duplicate and the cDNAs pooled to a final volume of 100 ul.

PCR Reactions:

Primary reaction (100 μl)
10 μl 10×buffer from Perkin Elmer Cetus GeneAmp kit
16 μl 1.25 mM each of dATP, dCTP, dGTP, dTTP
10 μl first strand TE-671 cDNA
2 μl 50 pmoles FS primer
2 μl 50 pmoles EM' primer
0.5 μl 2.5 units Amplitaq DNA polymerase
59.5 μl water Reaction conditions: 40 cycles of 90° C., 1'; 2' ramp to 45° C.; 2' at 45° C.; 2' at 72° oC.

Gel Purification

20 μl of the primary PCR reaction was purified on a 4% NuSieve agarose gel. The 180 base pair band was excised from the gel, heated to 65° C. for 5' and used directly as template for the secondary PCR reaction.

Secondary PCR reaction 200 μl
20 μl 10×buffer from Perkin Elmer Cetus GeneAmp kit
32 μl 1.25 mM each of dATP. dCTP, dGTP, dTTP
5 μl melted gel slice 4 µl 100 pmoles FS primer
4 µl 100 pmoles EM' primer
1 µl 5 units Amplitaq DNA polymerase
34 µl water Reaction conditions: 35 cycles of 94° C., 1'; 50° C., 2'; 72° C., 2'.

The PCR product was purified on a Qiagen tip 5 column, then digested with restriction endonuclease SalI. The SalI fragment was then ligated into SalI cut pGEM3Zf(+), and the ligation mix used to transform E. coli XL-1 blue. Plasmid DNA was isolated from white transformants and sequenced by the dideoxy chain termination method.

PCR Amplification, Cloning and Sequencing of p3'.19

Based on the sequence obtained from the pFSEM' clone, a specific PCR primer was synthesized; oligo LH 5' TTTGTCGACA CTG CAC TGT GTG CCG GTG 3' SEQ ID NO:23. This primer was used in combination with oligo A17, 5' GACTCGAGTCGACATCG 3' SEQ ID NO:24, to amplify the cDNA encoding the COOH terminus of the VEGF C subunit using the 3' RACE technique described by Frohman et al., PNAS 85: 8998–9002 (1988).

Poly A+ RNA was isolated from TE-671 cells using the Fast Track RNA isolation kit from Invitrogen and the protocol provided. First strand cDNA synthesis was performed as follows using the cDNA Cycle kit from Invitrogen and the TA17 adapter primer: TA17 5' GACTCGAGTCGA-CATCGATTTTTTTTTTTTTTTT 3' SEQ ID NO:5

0.8 µl 1 µg of TE-671 polyA+ RNA
20.7 µl water
5 µl 100 mM MeMgOH
6.25 µl 0.7 M B-mercaptoethanol
1.0 µl 0.88 µg primer TA17
2.5 µl RNase Inhibitor
10 µl 5×RT buffer
2.5 µl 25 mM dNTPs
1.25 µl reverse transcriptase 12.5 units The reaction was incubated for 60' at 42° C., then 3' at 95° C., placed on ice, then an additional 1.25 µl reverse transcriptase was added and the reaction incubated an additional 60' at 42° C.

3' RACE PCR
20 µl 10×buffer from Perkin Elmer Cetus GeneAmp kit
32 µl 1.25 mM each of dATP, dCTP, dGTP, dTTP
20 µl first strand TE-671 cDNA primed with TA17
2 µl 50 pmoles LH primer
2 µl 50 pmoles A17 primer
1.0 µl 5 units Amplitaq DNA polymerase
123 µl water Reaction conditions: 40 cycles of 94° C., 1'; 2' at 58° C.; 3' at 72° C.

The PCR product was purified on a Qiagen tip 5 column, then digested with restriction endonuclease SalI. The SalI fragment was then ligated into SalI cut pGEM3Zf(+), and the ligation mix used to transform E. coli XL-1 blue. Plasmid DNA was isolated from white transformants and sequenced by the dideoxy chain termination method.

PCR Amplification, Cloning and Sequencing of p5'.16

Based on the sequence obtained from the pFSEM' clone, two specific PCR primers were synthesized; oligo VE' 5' TTTGTCGACAACATTGGCCGTCTCCACC 3' SEQ ID NO:24, and oligo TG' 5' TTTGTCGACAATCGCCCAG-CAGCCGGT 3' SEQ ID NO:25. These primers were used in combination with oligo A17, 5' GACTCGAGTCGACATCG 3' SEQ ID NO:8, and oligo TA17 5'GACTCGAGTCGA-CATCGATTTTTTTTTTTTTTTT 3' SEQ ID NO:5 to amplify the cDNA encoding the amino terminus of the VEGF C subunit using the 5' RACE technique described by Frohman et al., PNAS 85: 8998–9002 (1988).

Poly A+ RNA was isolated from TE-671 cells using the Fast Track RNA isolation kit from Invitrogen and the protocol provided. First strand cDNA synthesis was performed as follows using the cDNA Cycle kit from Invitrogen and the VE' primer:

1.0 µl 1 µg of TE-671 polyA+ RNA
20.25 µl water
5 µl 100 mM MeMgOH
6.25 µl 0.7 M B-mercaptoethanol
1.0 µl 1.0 µg primer VE'
2.5 µl RNase Inhibitor
10 µl 5×RT buffer
2.5 µl 25 mM dNTPs
0.5 µl AMV reverse transcriptase (Promega) 10 units The reaction was incubated for 60' at 42° C., then 3' at 95° C., placed on ice, then an additional 1.25 ul reverse transcriptase was added and the reaction incubated an additional 60' at 42° C. Excess oligo VE' was removed by a Centricon 100 spin column and the 5' end of the cDNA was tailed by the addition of dATP and terminal transferase. The tailed cDNA was diluted to a final volume of 200 ul in 10 mM Tris-HCl, 1 mM EDTA, pH 7.5.

5' RACE PCR 5×100 ul
10 µl 10×buffer from Perkin Elmer Cetus GeneAmp kit
16 µl 1.25 mM each of dATP, dCTP, dGTP, dTTP
10 µl first strand TE-671 cDNA primed with VE'
2 µl 50 pmoles TG' primer
2 µl 50 pmoles A17 primer
2 µl 20 pmoles TA17 primer
0.5 µl 2.5 units Amplitaq DNA polymerase
57.5 µl water Reaction conditions: 40 cycles of 94° C., 1'; 2' ramp to 58° C.; 2' at 58° C.; 2' at 72° C.

The PCR product was purified on a Qiagen tip 5 column, then digested with restriction endonuclease SalI. The SalI fragment was then ligated into SalI cut pGEM3Zf(+), and the ligation mix used to transform E. coli XL-1 blue. Plasmid DNA was isolated from white transformants and sequenced by the dideoxy chain termination method. The combined sequences form plasmids pFSEM', p3'19 and p5'16 are shown in FIG. 9.

PCR Amplification, Cloning and Sequencing of phVC16 and phVC2

Based on the sequences of the p5'.16 and p3'.19 clones, two specific PCR primers were synthesized; oligo 5' GCVB 5' TTTGTCGAC TGG CTC TGG ACG TCT GAG 3' SEQ ID NO:26 and oligo 3'VC 5' TTTGTCGAC ACT GAA GAG TGT GAC GG 3' SEQ ID NO:27. These primers were used together to amplify the cDNA encoding the complete VEGF C subunit.

Poly A+ RNA was isolated from TE-671 cells using the Fast Track RNA isolation kit from Invitrogen and the protocol provided. First strand cDNA synthesis was performed as follows using the cDNA Cycle kit from Invitrogen;

0.8 µl 1 µg of TE-671 polyA+ RNA
19.2 µl water

5 μl 100 mM MeMgOH
6.25 μl 0.7 M B-mercaptoethanol
2.5 μl oligo dT primer
2.5 μl RNase Inhibitor
10 μl 5×RT buffer
2.5 μl 25 mM dNTPs
1.25 μl reverse transcriptase 12.5 units The reaction was incubated for 60' at 42° C., then 3' at 95° C., placed on ice, then an additional 1.25 ul reverse transcriptase was added and the reaction incubated an additional 60' at 42° C.

PCR Reaction 200 ul
20 μl 10×buffer from Perkin Elmer Cetus GeneAmp kit
32 μl 1.25 mM each of dATP, dCTP, dGTP, dTTP
20 μl first strand TE-671 cDNA primed with oligo dT
4 μl 50 pmoles 5' GCVB primer
4 μl 50 pmoles 3'VC primer
1 μl 5 units Amplitaq DNA polymerase
119 μl water Reaction conditions: 40 cycles of 94° C., 1'; 2' at 50° C.; 2' at 72° C.

The PCR product was purified on a Qiagen tip 5 column, then digested with restriction endonuclease SalI. The SalI fragment was then ligated into SalI cut pGEM3Zf(+), and the ligation mix used to transform E. coli XL-1 blue. Plasmid DNA was isolated from white transformants and sequenced by the dideoxy chain termination method. In the sequences of clones phVC16 and phVC2 base 463 (FIG. 9) was changed from a T to a C eliminating the translational stop codon following amino acid 154; this results in the addition of 16 amino acids following amino acid Lys 154. The nucleotide sequence and the deduced amino acid sequence of this addition is:

```
CAG AGA CCC ACA GAC TGC CAC CTG TGC GGC GAT GCT GTT   SEQ ID NOS: 28 & 29
Gln Arg Pro Thr Asp Cys His Leu Cys Gly Asp Ala Val
155                 160                 165

CCC CGG AGG TAA
Pro Arg Arg
        170
```

In addition clone phVC16 contains a 3 base pair deletion (FIG. 9, nucleotide residues 73–75) resulting in the deletion of Gln 25.

Cloning and Sequencing of an Alternative Form of VEGF C cDNA

Based on the sequences of the phVC16 and phVC2 clones, two specific PCR primers were synthesized: oligo 5'HVCE 5' TTTGAATTCCACC ATG CCG GTC ATG AGG CTG 3' SEQ ID NO:42 and oligo 3'HVCE 5' TTTGAATTC ACTGAAGAGTGTGACGG 3' SEQ ID NO:43. These primers were used together to amplify multiple cDNAs encoding alternative forms of the VEGF C subunit.

PCR Reaction 200 μl:
20 μl 10×buffer from Perkin Elmer Cetus GeneAmp kit
32 μl 0.25 mM each of dATP, dCTP, dGTP, dTTP
4 μl 25 pmoles 5'HVCE primer
4 μl 25 pmoles 3'HVCE primer
1 μl 5 units Amplitq DNA polymerase
133 μl water Reaction conditions: 40 cycles of 94° C., 1'; 2' to 50° C.; 2', 50° C.; 2', 72° C.

The PCR product was purified on a Qiagen Tip 5 column, precipitated by isopropanol, and digested with restriction endonuclease Eco RI. The Eco RI fragments were purified on a 1% agarose gel and then ligated into Eco RI cut pGEM3Zf(+). The ligation mix was used to transform E. coli XL-1 blue. Plasmid DNA was isolated from white transformants and sequenced by the dideoxy chain termination method. Two sets of clones were identified. Clone #A1 encoded the 170 amino acid form of VEGF C subunit identical to that shown in FIG. 10. Clone #B11 has a 63 base pair deletion between the second base of the $Arg^{141}$ codon and the third base of the $Leu^{162}$ codon. This clone encodes a 149 amino acid form of the VEGF C subunit, shown in FIG. 11.

EXAMPLE 12
Expression of VEGF AC Heterodimers in Insect Cells

Figure 13:
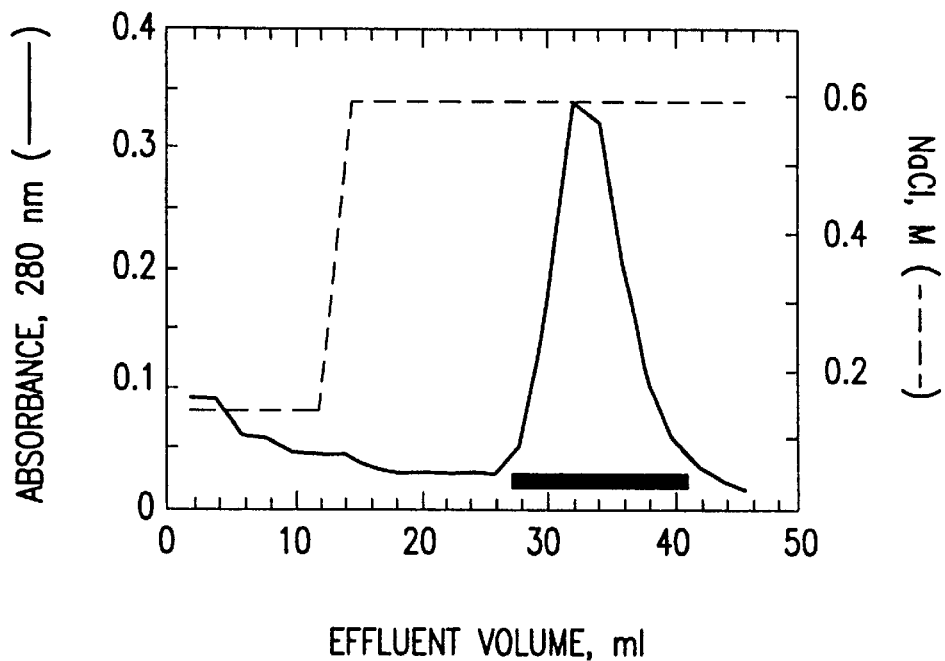
FIG. 13. Elution of VEGF from CM sephadex C50 is shown.

Conditioned medium from Sf9 insect cells co-infected with baculovirus containing DNA encoding human recombinant VEGF A (FIG. 12, 191 amino acid form) and VEGF C subunits (FIGS. 10 and 11, 126 amino acid form and 165 amino acid form) is thawed and brought to pH 6.0 with 1 N HCl. The medium contains VEGF AC heterodimers along with both VEGF AA and CC homodimers. The initial purification step of VEGF AC heterodimers consists of cation exchange chromatography using a variety of cation exchangers on a variety of matrices such as CM Sephadex, Pharmacia Mono S, Zetachrom SP and Polyaspartic Acid WCX (Nest Group), with the preferred exchanger being CM Sephadex C-50 (Pharmacia). The VEGF-containing medium is mixed with CM Sephadex C-50 that has been previously swollen and equilibrated in 0.05 M sodium phosphate, pH 6.0, at about 1 gram per liter of conditioned media. The mixture is stirred at low speed for about 1 hour at 4° C. The resin is then allowed to settle and the excess liquid is removed. The resin slurry is then washed with 0.05 M sodium phosphate, pH 6.0, containing 0.15 M NaCl to remove unbound and weakly bound protein from the resin. The resin slurry is then packed into a column and the remaining 0.15 M NaCl wash solution is removed. The VEGF is eluted with 0.05 M sodium phosphate, pH 6.0, containing 0.6 M NaCl (FIG. 13).

Figure 14:
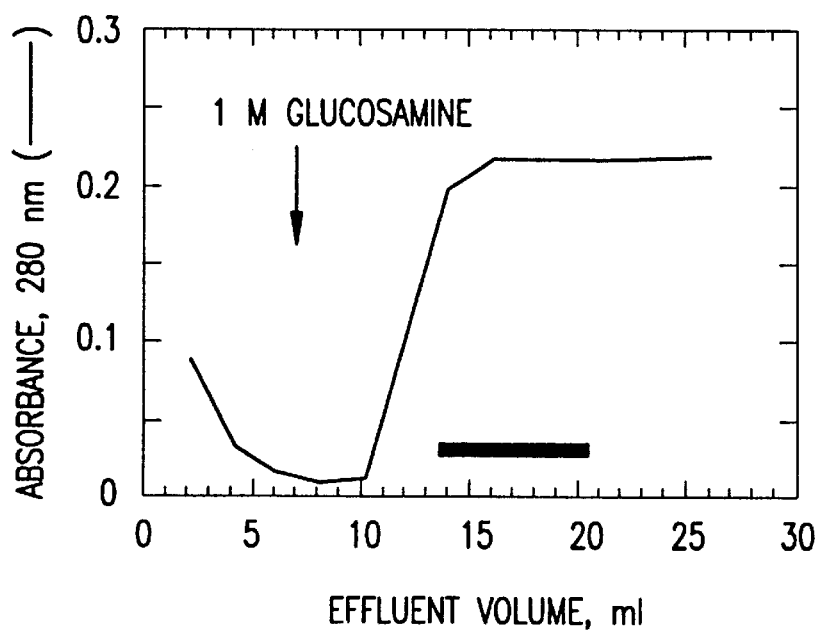
FIG. 14. Elution of VEGF from wheat germ agglutinin sepharose is shown.

The active fractions collected from the CM Sephadex C-50 column were further fractionated by lectin affinity chromatography for additional purification of VEGF AC. The lectins which may bind VEGF include, but were not limited to, those which specifically bind N-acetylglucosamine, with wheat germ agglutinin (WGA) being preferred. A 1.5 cm diameter column containing about 5 ml packed volume of WGA Sepharose (Pharmacia) is washed and equilibrated in 0.05 M sodium phosphate, pH 6.0, containing 0.5 M NaCl. The active fractions from the CM Sephadex C-50 column were pooled, the pH raised to 7.2 with 1 N NaOH and the active pool loaded onto the WGA column. The unbound protein is washed from the column with equilibration buffer and the VEGF is eluted with equilibration buffer containing 0.05 M sodium phosphate, pH 6.0, 0.15 M NaCl and 1.0 M N-acetyl-D-glucosamine (FIG. 14).

Figure 15:
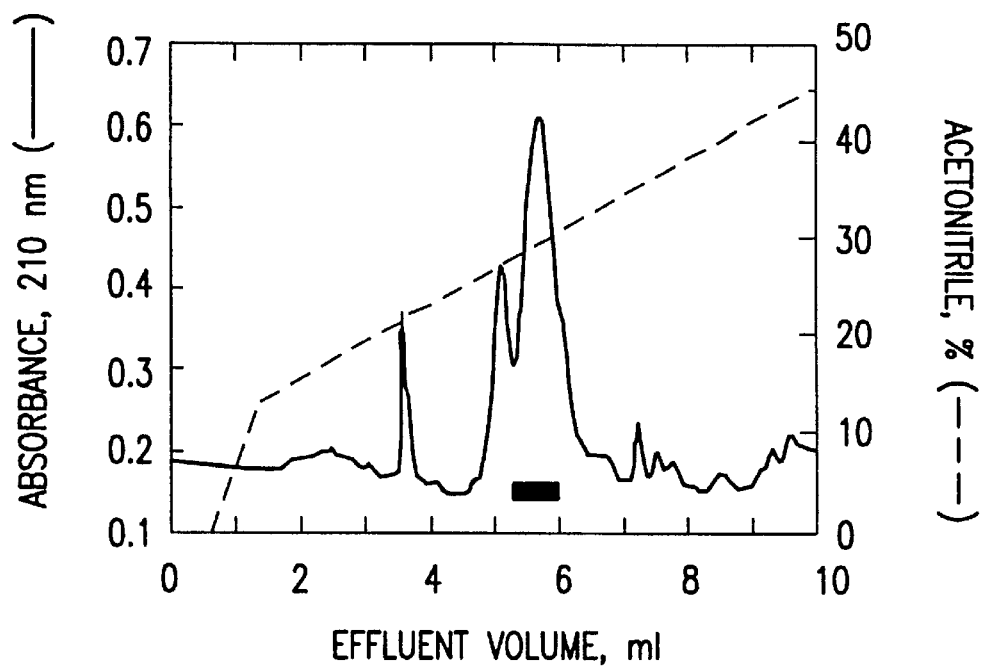
FIG. 15. Elution of VEGF AC heterodimer from reverse phase HPLC is shown
Figure 16:
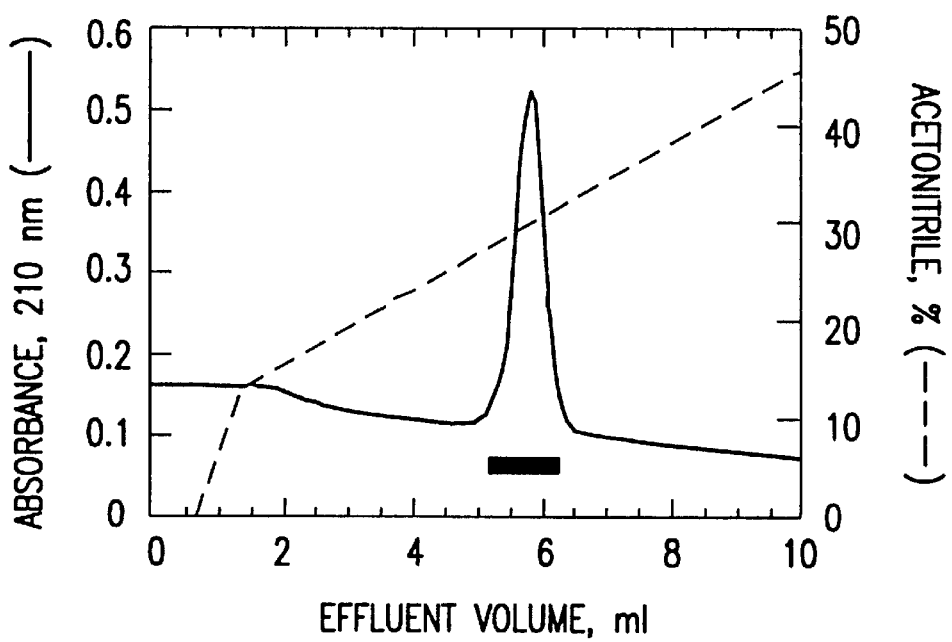
FIG. 16. Elution of pooled VEGF AC heterodimers from a reverse phase HPLC is shown.

The fractions containing VEGF activity eluted from the WGA column were loaded onto a 4.5×50 mm Vydac $C_4$ reverse phase HPLC column (The Separations Group) previously equilibrated in solvent A, 10 mM trifluoroacetic acid (TFA). The column is eluted with three sequential linear gradients of 0 to 20% B over 5 minutes, 20 to 70% B over 60 minutes and 70 to 100% B over 5 minutes, where B=33% A+67% acetonitrile (v/v). The flow rate is maintained at 0.5 ml/minute and individual peaks were manually collected. The VEGF AC heterodimer elutes with approximately 30% acetonitrile from the $C_4$ column under these conditions (FIG. 15). The pool containing VEGF AC is diluted with an equal volume of solvent A, reloaded onto the $C_4$ column (equilibrated in solvent A), and the column eluted with the above stated gradient. Individual peaks were manually collected. VEGF AC again elutes with approximately 30% acetonitrile as a single resolved symmetrical peak (FIG. 16).

Figure 17:
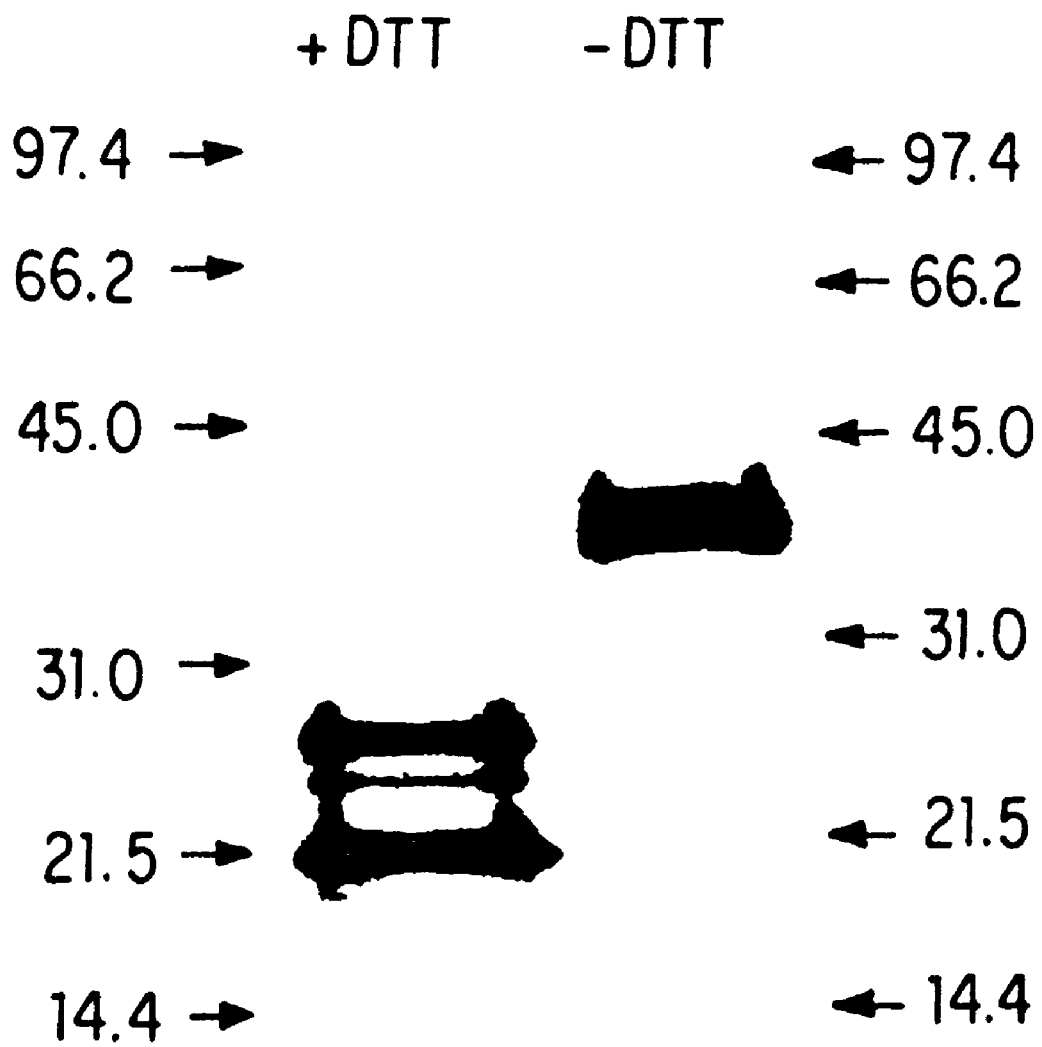
FIG. 17. A silver stained SDS-PAGE of VEGF AC with and without reducing agent is shown.

Purity of the protein is determined by sodium dodecyl-sulfate (SDS) polyacrylamide gel electrophoresis (PAGE) in 15% crosslinked gels using the technique of Laemmli, Nature 227: 680–684 (1970) under both reducing (+dithiothreitol) and nonreducing (−dithiothreitol) conditions. The silver stained gels (FIG. 17) show the VEGF AC heterodimer to consist of a single ~40 kDa band under non-reducing conditions. This apparent mass could be an underestimate of the true mass since, under nonreducing conditions, the protein can retain a rapidly migrating compact structure stabilized by intramolecular disulfide bonds. When a sample of VEGF is run on SDS-PAGE under reducing conditions, the heterodimer migrates as two major bands, with approximate masses of 25 and 20 kDa and a fainter band of 23 kDa. By comparison with pure VEGF A and C subunits and by Western analysis, VEGF A corresponds to the 25 kDa band and the weaker 23 kDa just below it. VEGF C migrates as the 20 kDa band.

Figure 18:
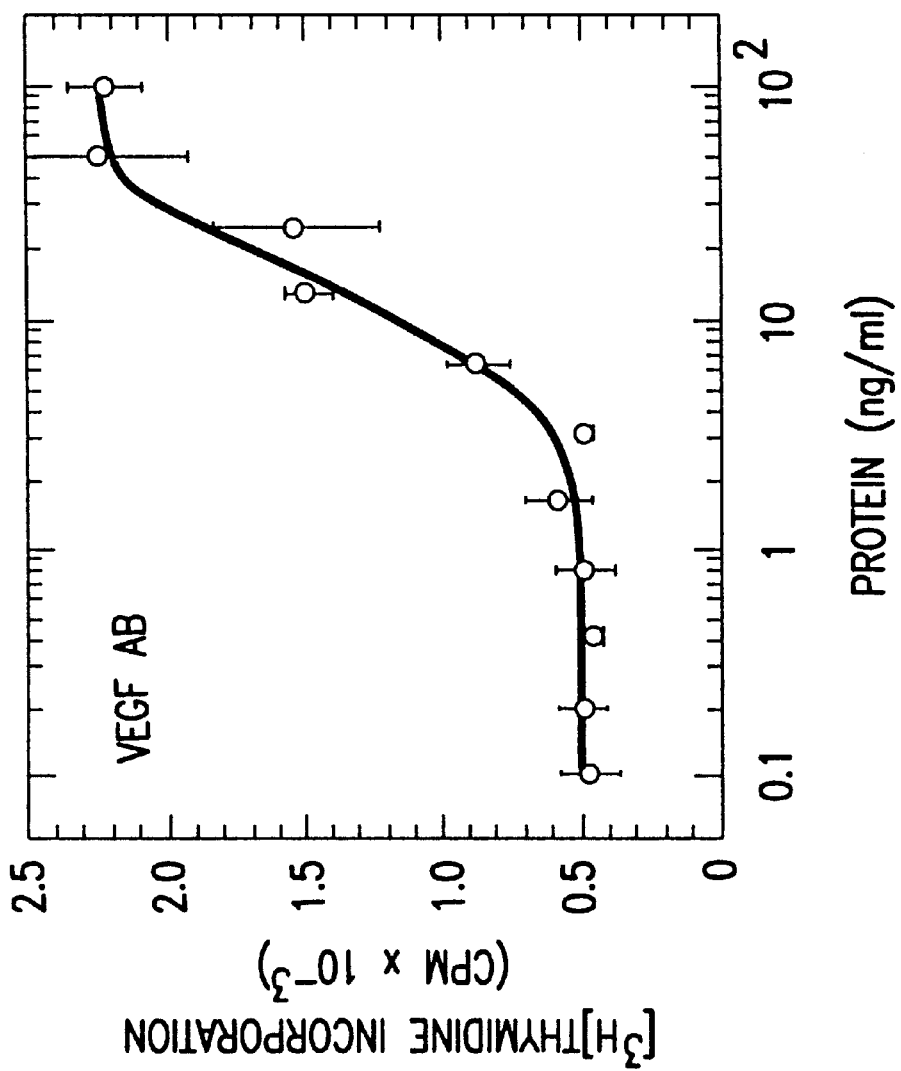
FIG. 18. The mitogenic activity of VEGF AC heterodimers on vascular endothelial cells is shown.

Biological activity is determined by mitogenic assay using human umbilical vein endothelial (HUVE) cells. HUVE cells were plated in gelatin-coated 96 well dishes at a density of about 12,000 cells per $cm^2$ in about 100 ml of Dulbecco's Modified Eagle's Media (DMEM) containing 10% heat-inactivated fetal calf serum (FCS) per well. The cells were incubated at 37° C. under 7.5% $CO_2$ for 24 hours. The medium was removed and 100 ml of fresh medium was added per well. Samples were serially diluted in DMEM containing 1 mg/ml bovine serum albumin (BSA) and added to the wells. After a further 24 hours of incubation, 80 μCi of [methyl-$^3$H]thymidine (20 Ci/mmol) and 25 μg of unlabeled thymidine per ml of medium was added to the wells in 10 ml of DMEM. The cells were incubated for 72 hours, washed with Hanks Balanced Salt Solution containing 1 mg/ml BSA and 25 mM HEPES buffer and lysed with 100 ml of a solution of 2 gm sodium carbonate and 0.4 gm NaOH per 100 ml. The amount of incorporation into cellular DNA was determined by scintillation counting. As shown in FIG. 18, pure recombinant human VEGF AC was mitogenic for human vascular endothelial cells with a half-maximal stimulation at ~10 ng/ml.

EXAMPLE 13

Expression of VEGF Heterodimers in Mammalian Cells

Eco RI cassettes of VEGF A and VEGF C were subcloned into the vectors pEE12 and pEE6 provided by Celltech to generate pEE12.hVEGF A, pEE12.hVEGF C and pEE6.hVEGF A. Restriction enzyme digests with Nco I/Bam HI (VEGF A) or Kpn I/Bam HI (VEGF C) were performed to verify that RNA of the proper orientation would be produced from the CMV promoter. In these vectors the VEGF cDNA is downstream of the human cytomegalovirus immediate early promoter (hCMVIE) and upstream of the SV40 polyadenylation signal. In order to generate heterodimers, pEE6.hVEGF A plasmid DNA was digested with Bam HI/Bgl II and the 3 Kb region consisting of the CMV promoter, VEGF A cDNA and the SV40 polyadenylation signal was isolated and purified. This 3 Kb region was isolated and ligated into the single Bam HI site of linearized pEE12.hVEGF C to yield a pEE12hVEGF C.hVEGF A. In this construct CMV promoters drive expression of VEGF A and VEGF C in tandem. Hind III digests were performed in order to verify the correct orientation.

In order to use these vectors to get expression of the VEGF subunits, vectors were linearized at the single Sal I site, and 30 μg electroporated into the murine myeloma cell line, NS/O. Stable cell lines were selected by their ability to grow in the absence of glutamine. All cell lines were screened for RNA production by northern analysis of poly (A)+mRNA prepared using the micro-FAST TRACK method from 2×10$^6$ cells. Western blot analysis confirmed the presence of VEGF protein.

SEQUENCE LISTING (1) GENERAL INFORMATION:

(iii) NUMBER OF SEQUENCES: 49

(2) INFORMATION FOR SEQ ID NO:1:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Ala Pro Thr Thr Glu Gly Glu Gln Lys Ala His Glu Val Val
    1               5                  10

(2) INFORMATION FOR SEQ ID NO:2:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:2:

Ala Leu Ser Ala Gly Asn Xaa Ser Thr Glu Met Glu Val Val Pro Phe
    1               5                  10                  15

Asn Glu Val (2) INFORMATION FOR SEQ ID NO:3:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

TTTGTCGACT TYATGGAYGT NTAYCA                                        26

(2) INFORMATION FOR SEQ ID NO:4:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

CAGAGAATTC GTCGACARTC NGTRTTYTTR CA                                 32

(2) INFORMATION FOR SEQ ID NO:5:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GACTCGAGTC GACATCGATT TTTTTTTTTT TTTTT                              35

(2) INFORMATION FOR SEQ ID NO:6:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TTTGTCGACT CAGAGCGGAG AAAGC                                         25

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TTTGTCGACG AAAATCACTG TGAGC                                         25

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GACTCGAGTC GACATCG                                                  17

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TTTGTCGACA ACACAGGACG GCTTGAAG                                      28

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TTTGTCGACA TACTCCTGGA AGATGTCC                                      28

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CTTCATCATT GCAGCAGC                                                 18

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTTGTCGACA ACCATGAACT TTCTGC                                              26

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

TTTGTCGACG GTGAGAGGTC TAGTTC                                              26

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TTTGTCGACA TAYATHGCNG AYGARC                                              26

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

TTTGTCGACT CRTCRTTRCA RCANCC                                              26

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

TTTGTCGACA CACCCTAATG AAGTGTC                                             27

(2) INFORMATION FOR SEQ ID NO:17:

(i) SEQUENCE CHARACTERISTICS:
        (A) LENGTH: 26 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

TTTGTCGACA ACAGCGACTC AGAAGG                                    26

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

TTTGTCGACA CTGAATATAT GAGACAC                                   27

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

TTTGTCGACNN GCAGGTCCTA GCTG                                     25

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TTTGTCGACN NCTAATAAAT AGAGGG                                    26

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TTTGTCGACA TTCAGTCCNT CNTGYGT                                   27

(2) INFORMATION FOR SEQ ID NO:22:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:22:

TTTGTCGACA CTGAGAGAAN GTCATYTC                                    28

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TTTGTCGACA CTGCACTGTG TGCCGGTG                                    28

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TTTGTCGACA ACATTGGCCG TCTCCACC                                    28

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TTTGTCGACA ATCGCCCAGC AGCCGGT                                     27

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TTTGTCGACT GGCTCTGGAC GTCTGAG                                     27

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TTTGTCGACA CTGAAGAGTG TGACGG                                      26

(2) INFORMATION FOR SEQ ID NO:28:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
CAGAGACCCA CAGACTGCCA CCTGTGCGGC GATGCTGTTC CCCGGAGGTA A         51
```

(2) INFORMATION FOR SEQ ID NO:29:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
    Gln Arg Pro Thr Asp Cys His Leu Cys Gly Asp Ala Val Pro Arg Arg
    1               5                  10                  15
```

(2) INFORMATION FOR SEQ ID NO:30:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
ATGAACTTTC TGCTCTCTTG GGTGCACTGG ACCCTGGCTT TACTGCTGTA CCTCCACCAT        60
GCCAAGTGGT CCCAGGCTGC ACCCACGACA GAAGGGGAGC AGAAAGCCCA TGAAGTGGTG       120
AAGTTCATGG ACGTCTACCA GCGCAGCTAT TGCCGTCCGA TTGAGACCCT GGTGGACATC       180
TTCCAGGAGT ACCCCGATGA GATAGAGTAT ATCTTCAAGC CGTCCTGTGT GCCCCTAATG       240
CGGTGTGCGG GCTGCTGCAA TGATGAAGCC CTGGAGTGCG TGCCCACGTC GGAGAGCAAC       300
GTCACTATGC AGATCATGCG GATCAAACCT CACCAAAGCC AGCACATAGG AGAGATGAGC       360
TTCCTGCAGC ATAGCAGATG TGAATGCAGA CCAAAGAAAG ATAGAACAAA GCCAGAAAAT       420
CACTGTGAGC CTTGTTCAGA GCGGAGAAAG CATTTGTTTG TCCAAGATCC GCAGACGTGT       480
AAATGTTCCT GCAAAAACAC AGACTCGCGT TGCAAGGCGA GGCAGCTTGA GTTAAACGAA       540
CGTACTTGCA GATGTGACAA GCCAAGGCGG TGA                                   573
```

(2) INFORMATION FOR SEQ ID NO:31:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
    Met Asn Phe Leu Leu Ser Trp Val His Trp Thr Leu Ala Leu Leu Leu
    1               5                  10                  15
```

```
        Tyr Leu His His Ala Lys Trp Ser Gln Ala Pro Thr Thr Glu Gly
                     20                  25                  30

Glu Gln Lys Ala His Glu Val Val Lys Phe Met Asp Val Tyr Gln Arg
                         35                  40                  45

Ser Tyr Cys Arg Pro Ile Glu Thr Leu Val Asp Ile Phe Gln Glu Tyr
         50                  55                  60

Pro Asp Glu Ile Glu Tyr Ile Phe Lys Pro Ser Cys Val Pro Leu Met
         65                  70                  75                  80

Arg Cys Ala Gly Cys Cys Asn Asp Glu Ala Leu Glu Cys Val Pro Thr
                             85                  90                  95

Ser Glu Ser Asn Val Thr Met Gln Ile Met Arg Ile Lys Pro His Gln
                        100                 105                 110

Ser Gln His Ile Gly Glu Met Ser Phe Leu Gln His Ser Arg Cys Glu
                        115                 120                 125

Cys Arg Pro Lys Lys Asp Arg Thr Lys Pro Glu Asn His Cys Glu Pro
        130                 135                 140

Cys Ser Glu Arg Arg Lys His Leu Phe Val Gln Asp Pro Gln Thr Cys
        145                 150                 155                 160

Lys Cys Ser Cys Lys Asn Thr Asp Ser Arg Cys Lys Ala Arg Gln Leu
                        165                 170                 175

Glu Leu Asn Glu Arg Thr Cys Arg Cys Asp Lys Pro Arg Arg
                        180                 185                 190

(2) INFORMATION FOR SEQ ID NO:32:

(i) SEQUENCE CHARACTERISTICS:
        (A) LENGTH: 445 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

ACCAATGAAC TTTCTGCTCT CTTGGGTGCA CTGGACCCTG GCTTTACTGC TGTACCTCCA         60

CCATGCCAAG TGGTCCCAGG CTGCACCCAC GACAGAAGGG GAGCAGAAAG CCCATGAAGT        120

GGTGAAGTTC ATGGACGTCT ACCAGCGCAG CTATTGCCGT CCGATTGAGA CCCTGGTGGA        180

CATCTTCCAG GAGTACCCCG ATGAGATAGA GTATATCTTC AAGCCGTCCT GTGTGCCCCT        240

AATGCGGTGT GCGGGCTGCT GCAATGATGA AGCCCTGGAG TGCGTGCCCA CGTCGGAGAG        300

CAACGTCACT ATGCAGATCA TGCGGATCAA ACCTCACCAA AGCCAGCACA TAGGAGAGAT        360

GAGCTTCCTG CAGCATAGCA GATGTGAATG CAGACCAAAG AAAGATAGAA CAAAGCCAGA        420

AAAATGTGAC AAGCCAAGGC GGTGA                                              445

(2) INFORMATION FOR SEQ ID NO:33:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

Met Asn Phe Leu Leu Ser Trp Val His Trp Thr Leu Ala Leu Leu
         1               5                  10                  15

Tyr Leu His His Ala Lys Trp Ser Gln Ala Ala Pro Thr Thr Glu Gly
                     20                  25                  30
```

```
        Glu Gln Lys Ala His Glu Val Val Lys Phe Met Asp Val Tyr Gln Arg
                35                  40                  45

Ser Tyr Cys Arg Pro Ile Glu Thr Leu Val Asp Ile Phe Gln Glu Tyr
                50                  55                  60

Pro Asp Glu Ile Glu Tyr Ile Phe Lys Pro Ser Cys Val Pro Leu Met
        65                  70                  75                  80

Arg Cys Ala Gly Cys Cys Asn Asp Glu Ala Leu Glu Cys Val Pro Thr
                            85                  90                  95

Ser Glu Ser Asn Val Thr Met Gln Ile Met Arg Ile Lys Pro His Gln
                    100                 105                 110

Ser Gln His Ile Gly Glu Met Ser Phe Leu Gln His Ser Arg Cys Glu
                    115                 120                 125

Cys Arg Pro Lys Lys Asp Arg Thr Lys Pro Glu Lys Cys Asp Lys Pro
        130                 135                 140

Arg Arg
        145

(2) INFORMATION FOR SEQ ID NO:34:

(i) SEQUENCE CHARACTERISTICS:
        (A) LENGTH: 649 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

AACCATGAAC TTTCTGCTCT CTTGGGTGCA CTGGACCCTG GCTTTACTGC TGTACCTCCA      60

CCATGCCAAG TGGTCCCAGG CTGCACCCAC GACAGAAGGG GAGCAGAAAG CCCATGAAGT     120

GGTGAAGTTC ATGGACGTCT ACCAGCGCAG CTATTGCCGT CCGATTGAGA CCCTGGTGGA     180

CATCTTCCAG GAGTACCCCG ATGAGATAGA GTATATCTTC AAGCCGTCCT GTGTGCCCCT     240

AATGCGGTGT GCGGGCTGCT GCAATGATGA AGCCCTGGAG TGCGTGCCCA CGTCGGAGAG     300

CAACGTCACT ATGCAGATCA TGCGGATCAA ACCTCACCAA AGCCAGCACA TAGGAGAGAT     360

GAGCTTCCTG CAGCATAGCA GATGTGAATG CAGACCAAAG AAAGATAGAA CAAAGCCAGA     420

AAAAAAATCA GTTCGAGGAA AGGGAAAGGG TCAAAAACGA AAGCGCAAGA AATCCCGGTT     480

TAAATCCTGG AGCGTTCACT GTGAGCCTTG TTCAGAGCGG AGAAAGCATT TGTTTGTCCA     540

AGATCCGCAG ACGTGTAAAT GTTCCTGCAA AAACACAGAC TCGCGTTGCA AGGCGAGGCA     600

GCTTGAGTTA AACGAACGTA CTTGCAGATG TGACAAGCCA AGGCGGTGA                649

(2) INFORMATION FOR SEQ ID NO:35:

(i) SEQUENCE CHARACTERISTICS:
        (A) LENGTH: 214 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

Met Asn Phe Leu Leu Ser Trp Val His Trp Thr Leu Ala Leu Leu Leu
        1               5                   10                  15

Tyr Leu His His Ala Lys Trp Ser Gln Ala Ala Pro Thr Thr Glu Gly
                    20                  25                  30

Glu Gln Lys Ala His Glu Val Val Lys Phe Met Asp Val Tyr Gln Arg
```

```
                    35                  40                  45
        Ser Tyr Cys Arg Pro Ile Glu Thr Leu Val Asp Ile Phe Gln Glu Tyr
            50                  55                  60

Pro Asp Glu Ile Glu Tyr Ile Phe Lys Pro Ser Cys Val Pro Leu Met
        65                  70                  75                  80

Arg Cys Ala Gly Cys Cys Asn Asp Glu Ala Leu Glu Cys Val Pro Thr
                        85                  90                  95

Ser Glu Ser Asn Val Thr Met Gln Ile Met Arg Ile Lys Pro His Gln
                    100                 105                 110

Ser Gln His Ile Gly Glu Met Ser Phe Leu Gln His Ser Arg Cys Glu
                115                 120                 125

Cys Arg Pro Lys Lys Asp Arg Thr Lys Pro Glu Lys Lys Ser Val Arg
        130                 135                 140

Gly Lys Gly Lys Gly Gln Lys Arg Lys Arg Lys Lys Ser Arg Phe Lys
        145                 150                 155                 160

Ser Trp Ser Val His Cys Glu Pro Cys Ser Glu Arg Arg Lys His Leu
                        165                 170                 175

Phe Val Gln Asp Pro Gln Thr Cys Lys Cys Ser Cys Lys Asn Thr Asp
                    180                 185                 190

Ser Arg Cys Lys Ala Arg Gln Leu Glu Leu Asn Glu Arg Thr Cys Arg
                195                 200                 205

Cys Asp Lys Pro Arg Arg
                210

(2) INFORMATION FOR SEQ ID NO:36:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

ATGCTGGCCA TGAAGCTGTT CACTTGCTTC TTGCAGGTCC TAGCTGGGTT GGCTGTGCAC        60

TCCCAGGGGG CCCTGTCTGC TGGGAACAAC TCAACAGAAA TGGAAGTGGT GCCTTTCAAT       120

GAAGTGTGGG GCCGCAGCTA CTGCCGGCCA ATGGAGAAGC TGGTGTACAT TGCAGATGAA       180

CACCCTAATG AAGTGTCTCA TATATTCAGT CCGTCATGTG TCCTTCTGAG TCGCTGTAGT       240

GGCTGCTGTG GTGACGAGGG TCTGCACTGT GTGGCGCTAA AGACAGCCAA CATCACTATG       300

CAGATCTTAA AGATTCCCCC CAATCGGGAT CCACATTCCT ACGTGGAGAT GACATTCTCT       360

CAGGATGTAC TCTGCGAATG CAGGCCTATT CTGGAGACGA CAAAGGCAGA AAGGTAA         417

(2) INFORMATION FOR SEQ ID NO:37:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Met Leu Ala Met Lys Leu Phe Thr Cys Phe Leu Gln Val Leu Ala Gly
        1               5                   10                  15

Leu Ala Val His Ser Gln Gly Ala Leu Ser Ala Gly Asn Asn Ser Thr
                    20                  25                  30
```

```
         Glu Met Glu Val Val Pro Phe Asn Glu Val Trp Gly Arg Ser Tyr Cys
                  35                  40                  45

Arg Pro Met Glu Lys Leu Val Tyr Ile Ala Asp Glu His Pro Asn Glu
                 50                  55                  60

Val Ser His Ile Phe Ser Pro Ser Cys Val Leu Leu Ser Arg Cys Ser
         65                  70                  75                  80

Gly Cys Cys Gly Asp Glu Gly Leu His Cys Val Ala Leu Lys Thr Ala
                             85                  90                  95

Asn Ile Thr Met Gln Ile Leu Lys Ile Pro Pro Asn Arg Asp Pro His
                         100                 105                 110

Ser Tyr Val Glu Met Thr Phe Ser Gln Asp Val Leu Cys Glu Cys Arg
                     115                 120                 125

Pro Ile Leu Glu Thr Thr Lys Ala Glu Arg
                 130                 135
```

(2) INFORMATION FOR SEQ ID NO:38:

(i) SEQUENCE CHARACTERISTICS:
        (A) LENGTH: 477 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

```
ATGCTGGCCA TGAAGCTGTT CACTTGCTTC TTGCAGGTCC TAGCTGGGTT GGCTGTGCAC      60

TCCCAGGGGG CCCTGTCTGC TGGGAACAAC TCAACAGAAA TGGAAGTGGT GCCTTTCAAT     120

GAAGTGTGGG GCCGCAGCTA CTGCCGGCCA ATGGAGAAGC TGGTGTACAT TGCAGATGAA     180

CACCCTAATG AAGTGTCTCA TATATTCAGT CCGTCATGTG TCCTTCTGAG TCGCTGTAGT     240

GGCTGCTGTG GTGACGAGGG TCTGCACTGT GTGGCGCTAA AGACAGCCAA CATCACTATG     300

CAGATCTTAA AGATTCCCCC CAATCGGGAT CCACATTCCT ACGTGGAGAT GACATTCTCT     360

CAGGATGTAC TCTGCGAATG CAGGCCTATT CTGGAGACGA CAAAGGCAGA AAGGAGGAAA     420

ACCAAGGGGA AGAGGAAGCA AAGCAAAACC CCACAGACTG AGGAACCCCA CCTGTGA       477
```

(2) INFORMATION FOR SEQ ID NO:39:

(i) SEQUENCE CHARACTERISTICS:
        (A) LENGTH: 158 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
         Met Leu Ala Met Lys Leu Phe Thr Cys Phe Leu Gln Val Leu Ala Gly
         1               5                   10                  15

Leu Ala Val His Ser Gln Gly Ala Leu Ser Ala Gly Asn Asn Ser Thr
                         20                  25                  30

Glu Met Glu Val Val Pro Phe Asn Glu Val Trp Gly Arg Ser Tyr Cys
                     35                  40                  45

Arg Pro Met Glu Lys Leu Val Tyr Ile Ala Asp Glu His Pro Asn Glu
                 50                  55                  60

Val Ser His Ile Phe Ser Pro Ser Cys Val Leu Leu Ser Arg Cys Ser
         65                  70                  75                  80

Gly Cys Cys Gly Asp Glu Gly Leu His Cys Val Ala Leu Lys Thr Ala
```

```
                   85                  90                  95
    Asn Ile Thr Met Gln Ile Leu Lys Ile Pro Pro Asn Arg Asp Pro His
                    100                 105                 110

Ser Tyr Val Glu Met Thr Phe Ser Gln Asp Val Leu Cys Glu Cys Arg
                115                 120                 125

Pro Ile Leu Glu Thr Thr Lys Ala Glu Arg Arg Lys Thr Lys Gly Lys
            130                 135                 140

Arg Lys Gln Ser Lys Thr Pro Gln Thr Glu Glu Pro His Leu
    145                 150                 155
```

(2) INFORMATION FOR SEQ ID NO:40:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

```
ATGCCGGTCA TGAGGCTGTT CCCTTGCTTC CTGCAGCTCC TGGCCGGGCT GGCGCTGCCT    60

GCTGTGCCCC CCCAGCAGTG GGCCTTGTCT GCTGGGAACG GCTCGTCAGA GGTGGAAGTG   120

GTACCCTTCC AGGAAGTGTG GGGCCGCAGC TACTGCCGGG CGCTGGAGAG GCTGGTGGAC   180

GTCGTGTCCG AGTACCCCAG CGAGGTGGAG CACATGTTCA GCCCATCCTG TGTCTCCCTG   240

CTGCGCTGCA CCGGCTGCTG CGGCGATGAG AATCTGCACT GTGTGCCGGT GGAGACGGCC   300

AATGTCACCA TGCAGCTCCT AAAGATCCGT TCTGGGGACC GGCCCTCCTA CGTGGAGCTG   360

ACGTTCTCTC AGCACGTTCG CTGCGAATGC CGGCCTCTGC GGGAGAAGAT GAAGCCGGAA   420

AGGAGGAGAC CCAAGGGCAG GGGGAAGAGG AGGAGAGAGA AGTAG                   465
```

(2) INFORMATION FOR SEQ ID NO:41:

(i) SEQUENCE CHARACTERISTICS:
        (A) LENGTH: 154 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

```
    Met Pro Val Met Arg Leu Phe Pro Cys Phe Leu Gln Leu Leu Ala Gly
    1               5                   10                  15

Leu Ala Leu Pro Ala Val Pro Pro Gln Gln Trp Ala Leu Ser Ala Gly
                20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
            50                  55                  60

Tyr Pro Ser Glu Val Glu His Met Phe Ser Pro Ser Cys Val Ser Leu
    65                  70                  75                  80

Leu Arg Cys Thr Gly Cys Cys Gly Asp Glu Asn Leu His Cys Val Pro
                    85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
                115                 120                 125
```

```
        Glu Cys Arg Pro Leu Arg Glu Lys Met Lys Pro Glu Arg Arg Arg Pro
            130                 135                 140

Lys Gly Arg Gly Lys Arg Arg Arg Glu Lys
        145                 150
```

(2) INFORMATION FOR SEQ ID NO:42:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

```
TTTGAATTCC ACCATGCCGG TCATGAGGCT G                              31
```

(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

```
TTTGAATTCA CTGAAGAGTG TGACGG                                    26
```

(2) INFORMATION FOR SEQ ID NO:44:

(i) SEQUENCE CHARACTERISTICS:
        (A) LENGTH: 513 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
ATGCCGGTCA TGAGGCTGTT CCCTTGCTTC CTGCAGCTCC TGGCCGGGCT GGCGCTGCCT    60

GCTGTGCCCC CCCAGCAGTG GGCCTTGTCT GCTGGGAACG GCTCGTCAGA GGTGGAAGTG   120

GTACCCTTCC AGGAAGTGTG GGGCCGCAGC TACTGCCGGG CGCTGGAGAG GCTGGTGGAC   180

GTCGTGTCCG AGTACCCCAG CGAGGTGGAG CACATGTTCA GCCCATCCTG TGTCTCCCTG   240

CTGCGCTGCA CCGGCTGCTG CGGCGATGAG AATCTGCACT GTGTGCCGGT GGAGACGGCC   300

AATGTCACCA TGCAGCTCCT AAAGATCCGT TCTGGGGACC GGCCCTCCTA CGTGGAGCTG   360

ACGTTCTCTC AGCACGTTCG CTGCGAATGC CGGCCTCTGC GGGAGAAGAT GAAGCCGGAA   420

AGGAGGAGAC CCAAGGGCAG GGGGAAGAGG AGGAGAGAGA AGCAGAGACC CACAGACTGC   480

CACCTGTGCG GCGATGCTGT TCCCCGGAGG TAA                               513
```

(2) INFORMATION FOR SEQ ID NO:45:

(i) SEQUENCE CHARACTERISTICS:
        (A) LENGTH: 170 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

```
        Met Pro Val Met Arg Leu Phe Pro Cys Phe Leu Gln Leu Leu Ala Gly
        1               5                   10                  15

Leu Ala Leu Pro Ala Val Pro Pro Gln Gln Trp Ala Leu Ser Ala Gly
                        20                  25                  30

Asn Gly Ser Ser Glu Val Glu Val Pro Phe Gln Glu Val Trp Gly
                    35                  40                  45

Arg Ser Tyr Cys Arg Ala Leu Glu Arg Leu Val Asp Val Val Ser Glu
                50                  55                  60

Tyr Pro Ser Glu Val Glu His Met Phe Ser Pro Ser Cys Val Ser Leu
        65                  70                  75                  80

Leu Arg Cys Thr Gly Cys Cys Gly Asp Glu Asn Leu His Cys Val Pro
                        85                  90                  95

Val Glu Thr Ala Asn Val Thr Met Gln Leu Leu Lys Ile Arg Ser Gly
                    100                 105                 110

Asp Arg Pro Ser Tyr Val Glu Leu Thr Phe Ser Gln His Val Arg Cys
                    115                 120                 125

Glu Cys Arg Pro Leu Arg Glu Lys Met Lys Pro Glu Arg Arg Arg Pro
                    130                 135                 140

Lys Gly Arg Gly Lys Arg Arg Glu Lys Gln Arg Pro Thr Asp Cys
        145                 150                 155                 160

His Leu Cys Gly Asp Ala Val Pro Arg Arg
                        165                 170
```

(2) INFORMATION FOR SEQ ID NO:46:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
ATGCCGGTCA TGAGGCTGTT CCCTTGCTTC CTGCAGCTCC TGGCCGGGCT GGCGCTGCCT       60

GCTGTGCCCC CCCAGCAGTG GGCCTTGTCT GCTGGGAACG GCTCGTCAGA GGTGGAAGTG      120

GTACCCTTCC AGGAAGTGTG GGGCCGCAGC TACTGCCGGG CGCTGGAGAG GCTGGTGGAC      180

GTCGTGTCCG AGTACCCCAG CGAGGTGGAG CACATGTTCA GCCCATCCTG TGTCTCCCTG      240

CTGCGCTGCA CCGGCTGCTG CGGCGATGAG AATCTGCACT GTGTGCCGGT GGAGACGGCC      300

AATGTCACCA TGCAGCTCCT AAAGATCCGT TCTGGGGACC GGCCCTCCTA CGTGGAGCTG      360

ACGTTCTCTC AGCACGTTCG CTGCGAATGC CGGCCTCTGC GGGAGAAGAT GAAGCCGGAA      420

AGGTGCGGCG ATGCTGTTCC CCGGAGGTAA                                      450
```

(2) INFORMATION FOR SEQ ID NO:47:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
        Met Pro Val Met Arg Leu Phe Pro Cys Phe Leu Gln Leu Leu Ala Gly
        1               5                   10                  15

Leu Ala Leu Pro Ala Val Pro Pro Gln Gln Trp Ala Leu Ser Ala Gly
                        20                  25                  30
```

```
        Asn Gly Ser Ser Glu Val Glu Val Pro Phe Gln Glu Val Trp Gly
                 35                  40                  45

Arg Ser Tyr Cys Arg Ala Leu Glu Arg Leu Val Asp Val Val Ser Glu
             50                  55                  60

Tyr Pro Ser Glu Val Glu His Met Phe Ser Pro Ser Cys Val Ser Leu
        65                  70                  75                  80

Leu Arg Cys Thr Gly Cys Cys Gly Asp Glu Asn Leu His Cys Val Pro
                         85                  90                  95

Val Glu Thr Ala Asn Val Thr Met Gln Leu Leu Lys Ile Arg Ser Gly
                    100                 105                 110

Asp Arg Pro Ser Tyr Val Glu Leu Thr Phe Ser Gln His Val Arg Cys
                    115                 120                 125

Glu Cys Arg Pro Leu Arg Glu Lys Met Lys Pro Glu Arg Cys Gly Asp
                130                 135                 140

Ala Val Pro Arg Arg
        145

(2) INFORMATION FOR SEQ ID NO:48:

(i) SEQUENCE CHARACTERISTICS:
        (A) LENGTH: 648 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 1..648

(xi) SEQUENCE DESCRIPTION: SEQ ID NO:48:

ATG AAC TTT CTG CTG TCT TGG GTG CAT TGG AGC CTT GCC TTG CTG CTC       48
Met Asn Phe Leu Leu Ser Trp Val His Trp Ser Leu Ala Leu Leu Leu
 1               5                  10                  15

TAC CTC CAC CAT GCC AAG TGG TCC CAG GCT GCA CCC ATG GCA GAA GGA       96
Tyr Leu His His Ala Lys Trp Ser Gln Ala Ala Pro Met Ala Glu Gly
             20                  25                  30

GGA GGG CAG AAT CAT CAC GAA GTG GTG AAG TTC ATG GAT GTC TAT CAG      144
Gly Gly Gln Asn His His Glu Val Val Lys Phe Met Asp Val Tyr Gln
         35                  40                  45

CGC AGC TAC TGC CAT CCA ATC GAG ACC CTG GTG GAC ATC TTC CAG GAG      192
Arg Ser Tyr Cys His Pro Ile Glu Thr Leu Val Asp Ile Phe Gln Glu
     50                  55                  60

TAC CCT GAT GAG ATC GAG TAC ATC TTC AAG CCA TCC TGT GTG CCC CTG      240
Tyr Pro Asp Glu Ile Glu Tyr Ile Phe Lys Pro Ser Cys Val Pro Leu
 65                  70                  75                  80

ATG CGA TGC GGG GGC TGC TGC AAT GAC GAG GGC CTG GAG TGT GTG CCC      288
Met Arg Cys Gly Gly Cys Cys Asn Asp Glu Gly Leu Glu Cys Val Pro
                 85                  90                  95

ACT GAG GAG TCC AAC ATC ACC ATG CAG ATT ATG CGG ATC AAA CCT CAC      336
Thr Glu Glu Ser Asn Ile Thr Met Gln Ile Met Arg Ile Lys Pro His
            100                 105                 110

CAA GGC CAG CAC ATA GGA GAG ATG AGC TTC CTA CAG CAC AAC AAA TGT      384
Gln Gly Gln His Ile Gly Glu Met Ser Phe Leu Gln His Asn Lys Cys
        115                 120                 125

GAA TGC AGA CCA AAG AAA GAT AGA GCA AGA CAA GAA AAA AAA TCA GTT      432
Glu Cys Arg Pro Lys Lys Asp Arg Ala Arg Gln Glu Lys Lys Ser Val
    130                 135                 140

CGA GGA AAG GGA AAG GGG CAA AAA CGA AAG CGC AAG AAA TCC CGG TAT      480
Arg Gly Lys Gly Lys Gly Gln Lys Arg Lys Arg Lys Lys Ser Arg Tyr
```

-continued

```
             145                 150                 155                 160
AAG TCC TGG AGC GTT CCC TGT GGG CCT TGC TCA GAG CGG AGA AAG CAT          528
Lys Ser Trp Ser Val Pro Cys Gly Pro Cys Ser Glu Arg Arg Lys His
                165                 170                 175

TTG TTT GTA CAA GAT CCG CAG ACG TGT AAA TGT TCC TGC AAA AAC ACA          576
Leu Phe Val Gln Asp Pro Gln Thr Cys Lys Cys Ser Cys Lys Asn Thr
                180                 185                 190

GAC TCG CGT TGC AAG GCG AGG CAG CTT GAG TTA AAC GAA CGT ACT TGC          624
Asp Ser Arg Cys Lys Ala Arg Gln Leu Glu Leu Asn Glu Arg Thr Cys
            195                 200                 205

AGA TGT GAC AAG CCG AGG CGG TGA                                          648
Arg Cys Asp Lys Pro Arg Arg  *
        210                 215
```

(2) INFORMATION FOR SEQ ID NO:49:

(i) SEQUENCE CHARACTERISTICS:
       (A) LENGTH: 215 amino acids
       (B) TYPE: amino acid
       (D) TOPOLOGY: linear (ii) MOLECULE TYPE: protein (xi) SEQUENCE DESCRIPTION: SEQ ID NO:49:

```
Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
            195                 200                 205

Arg Cys Asp Lys Pro Arg Arg
        210                 215
```

What is claimed is:

1. Human Vascular endothelial cell growth factor AC comprising an A subunit amino acid sequence and a C subunit amino acid sequence.

2. Human Vascular endothelial cell growth factor BC comprising an B subunit amino acid sequence and a C subunit amino acid sequence.

3. A purified and isolated vascular endothelial cell growth factor C subunit amino acid sequence comprising:

```
Met Pro Val Met Arg Leu Phe Pro Cys Phe Leu Gln Leu Leu    SEQ ID NOS:45

Ala Gly Leu Ala Leu Pro Ala Val Pro Pro Gln Gln Trp Ala

Leu Ser Ala Gly Asn Gly Ser Ser Glu Val Glu Val Val Pro

Phe Gln Glu Val Trp Gly Arg Ser Tyr Cys Arg Ala Leu Glu

Arg Leu Val Asp Val Val Ser Glu Tyr Pro Ser Glu Val Glu

His Met Phe Ser Pro Ser Cys Val Ser Leu Leu Arg Cys Thr

Gly Cys Cys Gly Asp Glu Asn Leu His Cys Val Pro Val Glu

Thr Ala Asn Val Thr Met Gln Leu Leu Lys Ile Arg Ser Gly

Asp Arg Pro Ser Tyr Val Glu Leu Thr Phe Ser Gln His Val

Arg Cys Glu Cys Arg Pro Leu Arg Glu Lys Met Lys Pro Glu

Arg Arg Arg Pro Lys Gly Arg Gly Lys Arg Arg Arg Glu Lys

Gln Arg Pro Thr Asp Cys His Leu Cys Gly Asp Ala Val Pro

Arg Arg.
```

4. A tissue repairing pharmaceutical composition comprising a pharmaceutical carrier and an effective tissue repairing amount of the purified vascular endothelial growth factor of claim 1.

5. A tissue repairing pharmaceutical composition comprising a pharmaceutical carrier and an effective tissue repairing amount of the purified vascular endothelial cell growth factor of claim 2.

6. A purified human vascular endothelial cell growth factor CC comprising a first C subunit amino acid sequence and a second C subunit amino acid sequence, wherein said first and said second C subunit comprise the amino acid sequence as set forth in SEQ ID NO:45.

7. A tissue repairing pharmaceutical composition comprising a pharmaceutical carrier and an effective tissue repairing amount of purified vascular endothelial growth factor of claim 6.

* * * * *